US008048416B2

(12) United States Patent
Young et al.

(10) Patent No.: US 8,048,416 B2
(45) Date of Patent: *Nov. 1, 2011

(54) CYTOTOXICITY MEDIATION OF CELLS EVIDENCING SURFACE EXPRESSION OF CD44

(75) Inventors: David S. F. Young, Toronto (CA); Daad Sayegh, Mississauga (CA); Sheung Tat Fan, Hong Kong (CN); Ronnie Tung Ping Poon, Hong Kong (CN); Terence Kin Wah Lee, Hong Kong (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 130 days.

This patent is subject to a terminal disclaimer.

(21) Appl. No.: 11/786,165

(22) Filed: Apr. 11, 2007

(65) Prior Publication Data
US 2007/0248538 A1 Oct. 25, 2007

Related U.S. Application Data

(63) Continuation-in-part of application No. 11/716,216, filed on Mar. 9, 2007, now abandoned, which is a continuation-in-part of application No. 11/364,013, filed on Feb. 28, 2006, now Pat. No. 7,947,496, which is a continuation-in-part of application No. 10/810,165, filed on Mar. 26, 2004, now abandoned, which is a continuation-in-part of application No. 10/647,818, filed on Aug. 22, 2003, now Pat. No. 7,187,397, which is a continuation-in-part of application No. 10/603,000, filed on Jun. 23, 2003, now Pat. No. 7,252,821, which is a continuation-in-part of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
*A61K 39/395* (2006.01)
*A61K 39/44* (2006.01)

(52) U.S. Cl. ............... 424/133.1; 424/144.1; 424/178.1

(58) Field of Classification Search ............ 424/133.1, 424/144.1, 178.1
See application file for complete search history.

(56) References Cited

U.S. PATENT DOCUMENTS

| | | | |
|---|---|---|---|
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,693,322 A | 12/1997 | Creekmore et al. | |
| 5,693,763 A | 12/1997 | Codington et al. | |
| 5,750,102 A | 5/1998 | Eisenbach et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 7,189,397 B2 * | 3/2007 | Young et al. | 424/156.1 |
| 7,252,821 B2 * | 8/2007 | Young et al. | 424/141.1 |
| 7,507,537 B2 * | 3/2009 | Young et al. | 435/6 |
| 2001/0003777 A1 | 6/2001 | Young et al. | |
| 2001/0009665 A1 | 7/2001 | Young et al. | |
| 2002/0051780 A1 | 5/2002 | Lindhofer et al. | |
| 2002/0160010 A1 | 10/2002 | Herrlich et al. | |
| 2003/0103985 A1 | 6/2003 | Adolf et al. | |
| 2004/0001789 A1 | 1/2004 | Young et al. | |
| 2004/0101530 A1 | 5/2004 | Young et al. | |
| 2006/0269481 A1 | 11/2006 | Young et al. | |
| 2008/0131429 A1 * | 6/2008 | Young et al. | 424/133.1 |
| 2008/0219919 A1 * | 9/2008 | Young et al. | 424/1.49 |
| 2009/0004103 A1 * | 1/2009 | Young et al. | 424/1.49 |

FOREIGN PATENT DOCUMENTS

| | | |
|---|---|---|
| WO | WO9412631 | 6/1994 |
| WO | WO9520401 | 8/1995 |
| WO | WO0294879 | 5/2002 |
| WO | WO02082076 | 10/2002 |
| WO | WO03055515 | 7/2003 |
| WO | WO2004087205 | 10/2004 |

OTHER PUBLICATIONS

Haramaki et al. (Hepatol. 21(5): 1276-1284 (1995) Abstract.*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Breyer, R. et al., "Disruption of intracerebral progression of C6 rat glioblastoma by in vivo treatment with anti-CD44 monoclonal antibody", J. Neurosurg., 92: 140-149, (Jan. 2000).
Zawadzki et al., "Blockade of Meatasis Formation by CD44-Receptor Globulin", Int. J. Cancer, 75: 919-924 (1998).
Zahalka et al., "Lymph Node (but Not Spleen) Invasion by Murine Lymphoma Is Both CD44- and Hyaluronate-Dependent", The Journal of Immunology, 154: 5345-5355 (1995).

(Continued)

*Primary Examiner* — Lynn Bristol
(74) *Attorney, Agent, or Firm* — Fish & Richardson P.C.

(57) ABSTRACT

This invention relates to the diagnosis and treatment of cancerous diseases, particularly to the mediation of cytotoxicity of primary and metastatic human tumor cells; and most particularly to the use of an isolated monoclonal antibody or cancerous disease modifying antibodies (CDMAB) thereof, optionally in combination with one or more chemotherapeutic agents, as a means for initiating the cytotoxic response in human tumors, e.g. any primary or metastatic tumor sites which arise from hepatocytes and to binding assays which utilize the CDMAB of the instant invention.

16 Claims, 7 Drawing Sheets
(3 of 7 Drawing Sheet(s) Filed in Color)

OTHER PUBLICATIONS

Wallach-Dayan et al., "CD44-dependent lymphoma cell dissemination: a cell surface supports in vitro lymphoma cell rolling on hyaluronic acid substrate and its in vitro accumulation in the peripheral lymph nodes", Journal of Cell Science, 114: 3463-3477 (2001).
Strobel et al., "In vivo Inhibition of CD44 Limits Intra-Abdominal Spread of Human Ovarian Cancer Xenograft in Nude Mice: A Novel Role for CD44 in the Process of Peritoneal Implantation" Cancer Research, 57:1228-1232 (Apr. 1, 1997).
M. Allouche et al, "Ligation of the CD44 adhesion molecule inhibits drug-induced apoptosis in human myeloid leukemia cells", Blood, 96(3):1187-1190 (Aug. 2000).
C. Badger et al, "Prospects for monoclonal antibody therapy of leukemia and lymphoma", Cancer, 58:584-589 (1986).
I. Barshack et al, "CD44 expression in normal adrenal tissue and adrenal tumors", J. Clin. Pathol., 51:52-54 (1998).
A. Begg et al, "Rapid fluorescence-based assay for radiosensitivity and chemosensitivity testing in mammalian cells in vitro", Cancer Research, 49:565-569 (Feb. 1989).
Becton Dickinson Technical Data Sheet for L178 Clone (published Nov. 5, 2003).
E. Boven et al, "Monoclonal antibodies in cancer treatment: where do we stand after 10 years?", Radiotherapy and Oncology, 5:109-117 (1986).
M. Chatterjee et al, "Idiotypic antibody immunotherapy of cancer", Cancer Immunol. Imunother, 38:75-82 (1994).
M. Co et al, "Chimeric and humanized antibodies with specificity for the CD33 antigen", J. Immunol., 148:1149-1154 (Feb. 1992).
D. Colnot et al, "Reinfusion of unprocessed, granulocyte colony-stimulating factor-stimulated whole blood allows dose escalation of 186relabeled chimeric monoclonal antibody U36 radioimmunotherapy in a phase I dose escalation study", Clin. Cancer Res., 8:3401-3406 (Nov. 2002).
D. Colnot et al, "Radioimmunotherapy in patients with head and neck squamous cells carcinoma:initial experience", Head & Neck, 23:559-565 (Jul. 2001).
D. Colnot et al, "Phase I therapy study of 186Re-labeled chimeric monoclonal antibody U36 in patients with squamous cell carcinoma of the head and neck", J. Nucl. Med., 41:1999-2010 (Dec. 2000).
D. Colnot et al, "Evaluation of limited blood sampling in a preceding 99mTC-labeled diagnostic study to predict the pharmacokinetics and myelotoxicity of 186Re-cMAb U36 radioimmunotherapy", J. Nucl. Med., 42(9):1364-1367 (Sep. 2001).
A. Costa et al, "Implications of disaggregation procedures on biological representation of human solid tumours", Cell Tisue Kinet., 20:171-180 (1987).
J. Cruse et al, Illustrated Dictionary of Immunology, CRC Press, p. 280 (1995).
B. Curti, "Physical barriers to drug delivery in tumors", Critical Reviews in Oncology/Hematology, 14:29-39 (1993).
A. Daar et al, "The membrane antigens of human colorectal cancer cells:demonstration with monoclonal antibodies of heterogeneity within and between tumours and of anomalous expression of HLA-DR", Eur. J. Cancer Clin. Oncol., 19(2):209-220 (1983).
S. Dairkee et at, "Partial enzymatic degradation of stroma allows enrichment and expansion of primary breast tumor cells", Cancer Research, 57:1590-1596 (Apr. 1997).
R. De Bree et al, "Selection of monoclonal antibody E48 IgG or U36 IgG for adjuvant radioimmunotherapy in head and neck cancer patients", British J. Cancer, 75(7):1049-1060 (1997).
R. De Bree et al, Radioimmunoscintigraphy and biodistribution of technetium-99m-labeled monoclonal antibody U36 in patients with head and neck cancer, Clin. Can. Res., 1:591-598 (Jun. 1995).
S. Denning et al, "Antibodies against the CD44 p80, lymphocyte homing receptor molecule augment human peripheral blood T cell activation", J. Immunol., 144:7-15 (Jan. 1990).
G. Dermer, "Another anniversary for the war on cancer", Bio/Technology, 12:320 (Mar. 1994).
R. Dillman, "Antibodies as cytotoxic therapy", J. Clin. Oncol., 12(7):1497-1515 (Jul. 1994).
R. Dillman, "Monoclonal antibodies for treating cancer", Annals of Internal Medicine, 111:592-603 (1989).
M. Disis et al, "HER-2/neu protein: a target for antigen-specific immunotherapy of human cancer", Advances in Cancer Research, 71:343-371 (1997).
H. Drexler, "Recent results on the biology of Hodgkin and Reed-Sternberg cells", Leukemia and Lymphoma, 9:1-25 (1993).
Eckhardt et al., "Developmental Therapeutics: Successes and Failures of Clinical Trial Designs of Targeted Compounds"; ASCO Educational Book, 39th Annual Meeting, 2003, pp. 209-219.
M. Embleton, "Monoclonal antibodies to osteogenic sarcoma antigens", Immunol. Ser., 23:181-207 (1984).
S. Engelholm et al, "Disaggregation of human solid tumours by combined mechanical and enzymatic methods", Br. J. Cancer, 51:93-98 (1985).
A. Epstein et al, "Two new monoclonal antibodies, Lym-1 and Lym-2, reactive with human B-lymphocytes and derived tumors, with immunodiagnostic and immunotherapeutic potential", Cancer Research, 47:830-840 (1987).
B. Flanagan et al, "Chemical composition and tissue distribution of the human CDw44 glycoprotein", Immunol., 67:167-175 (Mar. 1989).
K. Foon, "Biological therapy of cancer", Breast Cancer Research & Treatment, 7:5-14 (1986).
S. Fox et al, "Normal human tissues, in addition to some tumors, express multiple different CD44 isoforms", Cancer Res., 54:4539-4546 (Aug. 1994).
R. Freshney, "Culture of animal cells", a Manual of Basic Technique, Alan R. Liss, Inc., New York, p. 3 (1983).
H. Dvorak et al, "Structure of solid tumors and their vasculature: implications for therapy with monoclonal antibodies", Cancer Cells, 3(3):77-85 (Mar. 1991).
B. Franzen et al, "Nonenzymatic extraction of cells from clinical tumor material for analysis of gene expression by two-dimensional polyacrylamide gel electrophoresis", Electrophoresis, 14:1045-1053 (1993).
J. Berzoksky et al, "Chapter 8: Immunology and antigen structure", in Fundamental Immunology, p. 242, ed. William E. Paul M.D., 3d ed. Raven Press, NY (1993).
R. Galandrini et al, CD44 Triggering enhances human NK cell cytotoxic functions, Journal of Immunology, 153:4399-4407 (1994).
U. Gunthert et al, "A new variant of glycoprotein CD44 confers metastatic potential to rat carcinoma cells", Cell, 65:13-24 (Apr. 1991).
Y. Guo et al, "Inhibition of human melanoma growth and metastasis in vivo by anti-CD44 monoclonal antibody", Cancer Res., 54:1561-1565 (Mar. 1994).
T. Gura, "Systems for identifying new drugs are often faulty", Science, 278:1041-1042 (Nov. 1997).
L. Hartwell et al, "Integrating genetic approaches into the discovery of anticancer drugs", Science, 278:1064-1068 (Nov. 1997).
D. Harris et al, "Serotherapy of cancer", Seminars in Oncology, 16(3):180-198 (Jun. 1989).
K. Heider et al, "Differential expression of CD44 splice variants in intestinal- and diffuse-type human gastric carcinomas and normal gastric mucosa", Cancer Res., 53:4197-4203 (Sep. 1993).
K. Heider et al, "A human homologue of the rat metastasis-associated variant of CD44 is expressed in colorectal carcinomas and adenomatous polyps", J. Cell Biol., 120:27-233 (Jan. 1993).
K. Heider et al, "Splice variants of the cell surface glycoprotein CD44 associated with metastatic tumour cells are expressed in normal tissues of humans and cynomolgus monkeys", Eur. J. Cancer, 31A(13/14):2385-2391 (1995).
D. Herlyn et al, "Monoclonal anticolon carcinoma antibodies in complement-dependent cytotoxicity", Int. J. Cancer, 27:769-774 (1981).
S. Hirschfeld et at, "Oncology drug development: United States Food and Drug Administration perspective", Critical Reviews in Oncology/Hematology 42:137-143 (2002).
J. Horoszewicz et al, "Monoclonal antibodies to a new antigenic marker in epithelial prostatic cells and serum of prostatic cancer patients", Anticancer Research, 7:927-936 (1987).
E. Holz et al, "Antibody-based immunotherapeutic strategies in colorectal cancer", Recent Results in Cancer Research, 142:381-400 (1996).

T. Hsu, "Karyology of cells in culture—a preparation and analysis of karyotypes and idiograms", in Tissue Culture Methods and Applications, eds. Kruse and Patterson, Academic Press, New York, pp. 764-767 (1973).

R. Jain, "Barriers to drug delivery in solid tumors", Scientific American, 271(1):58-65 (Jul. 1994).

R. Johnson et al, "The clinical impact of screening and other experimental tumor studies", Cancer Treatment Review, 2:1-31 (1975).

S. Jalkanen et al, "Biochemical properties of glycoproteins involved in lymphocyte recognition of high endothelial venules in man", J. Immunol., 141:1615-1623 (Sep. 1988).

S. Kayastha et al, "Expression of the hyaluronan receptor, CD44S, in epithelial ovarian cancer is an independent predictor of survival", Clin. Cancer Res., 5:1073-1076 (May 1999).

S. Kennel et al, "CD44 expression on murine tissues", J. Cell Science, 104:373-382 (1993).

M. Khoursheed et al, "Expression of CD44s in human colorectal cancer", Pathology Oncology Research, 8(3):170-174 (2002).

A. Knuth et al, "ADCC reactivity of human melanoma cells with mouse monoclonal antibodies", Proc. Am. Assoc. Cancer Res., 25:1005 (Mar. 1984) Abstract only.

G. Koopman et al, "Activated human lymphocytes and aggressive non-hodgkin's lymphomas express a homologue of the rat metastasis-associated variant of CD44", J. Exp. Med., 177:897-904 (Apr. 1993).

V. Kravtsov et al, "Automated monitoring of apoptosis in suspension cell cultures", Laboratory Investigation, 74(2):557-570 (1996).

M. Kuppner et al, "Differential expression of the CD44 molecule in human brain tumours", Int. J. Cancer, 50:572-577 (1992).

C. Mackay et al, "Expression and modulaton of CD44 variant isoforms in humans", J. Cell Biol., 124:71-82 (Jan. 1994).

D. Naor et al, "CD44 in cancer", Critical Reviews in Clinical Laboratory Science, 39(6):527-579 (2002).

H. Ponta et al, "CD44: from adhesion molecules to signaling regulators", Nature Reviews, Molecular Cell Biology, 4:33-45 (Jan. 2003).

J. Ross et al, "Expression of the CD44 cell adhesion molecule in urinary bladder transitional cell carcinoma", Mod. Pathol., 9(8):854-860 (1996).

S. Rudikoff et al, "Single amino acid substitution altering antigen-binding specificity", Proc Natl Acad Sci USA, 79:1979-1983 (Mar. 1982).

M. Sami et al, "Regulated expression of exon v6 containing isoforms of CD44 in man: downregulation during malignant transformation of tumors of squamocellular origin", J. Cell Biol., 122(2):431-442 (Jul. 1993).

A. Schrijvers et al, "MAb U36, a novel monoclonal antibody successful in immunotargeting of squamous cell carcinoma of the head and neck", Cancer Res., 53:4383-4390 (Sep. 1993).

S. Seaver, "Monoclonal antibodies in industry: more difficult than originally thought", Genetic Engineering News, 14(14):10 and 21 (1994).

S. Seiter et al, "Prevention of tumor metastasis formation by anti-variant CD44", J. Exp. Med., 177:443-455 (Feb. 1993).

A. Seth et al, "T-cell-receptor-independent activation of cytolytic activity of cytotoxic T lymphocytes mediated through CD44 and gp9OMEL-14", Proc. Nat'l Acad Sci. USA, 88:7877-7881 (Sep. 1991).

Y. Shimizu et al, "Dual role of the CD44 molecule in T cell adhesion and activation", J. Immunol., 143:2457-2463 (Oct. 1989).

J. Stroomer et al, "Safety and biodistribution of 99m Technetium-labeled anti-CD44v6 monoclonal antiody BIWA 1 in head and neck cancer patients", Clin. Can. Res., 6:3046-3055 (Aug. 2000).

P. Therasse et al, New guidelines to evaluate the response to treatment in solid tumors, Journal of the National Cancer Institute, 92(3):205-216 (Feb. 2000).

N. Van Hal et al, "Monoclonal antibody U36, a suitable candidate for clinical immunotherapy of squamous-cell carcinoma, recognizes a CD44 isoform", Int. J. Cancer, 68:520-527 (1996).

D. Young et at., "ARH460-16-2: A Therapeutic Monoclonal Antibody Targeting CD44 in HER2/neu Negative Breast cancer", Journal of Clinical Oncology, 22: 193s (Jul. 2004) Abstract 2622.

G. Kohler et al, "Continuous cultures of fused cells secreting antibody of predefined specificity", Nature, 256: 495-497 (Aug. 1975).

Paul, "Fundamental Immunology", 3rd Edition, 1993, pp. 242.

Johnson et al., "The Clinical Impact of Screening and Other Experimental Tumor Studies", Cancer Treatment Review (1975), vol. 2, pp. 1-31.

Heider et al., "Characterization of a High-Affinity Monoclonal Antibody Specific for CD44v6 as Candidate for Immunotherapy of Squamous Cell Carcinomas", Cancer Immunol Immunother (1996), vol. 43, pp. 245-253.

Campbell et al., "Biology: 5th Edition", 1999, p. 856.

Oostendorp et al., "Evidence for Differences in the Mechanisms by which Antibodies Against CD44 Promote Adhesion of Erythroid and Granulopoietic Progenitors to Marrow Stromal Cells", British Journal of Haematology (1998), vol. 101, pp. 436-445.

Naor et al., "CD44: Structure, Function, and Association with the Malignant Process", Advances in Cancer Research (1997), vol. 71, pp. 241-319.

Co et al., "Humanized Antibodies for Therapy", Nature (1991), vol. 351, pp. 501-502.

Examination report dated Jun. 17, 2008 for U.S. Appl. No. 11/774,293.

Examination report dated Mar. 20, 2009 for U.S. Appl. No. 11/777,551.

Examination report dated Apr. 10, 2009 for U.S. Appl. No. 11/774,293.

Examination report dated Apr. 22, 2009 for U.S. Appl. No. 11/879,676.

Examination report dated Jun. 4, 2009 for U.S. Appl. No. 11/880,619.

Examination report dated Jun. 12, 2009 for U.S. Appl. No. 12/284,137.

Examination report dated Jun. 16, 2009 for U.S. Appl. No. 12/055,014.

Examination report dated Jul. 1, 2009 for U.S. Appl. No. 11/938,841.

Examination report dated Jul. 15, 2009 for U.S. Appl. No. 12/017,827.

Examination report dated Jul. 17, 2009 for U.S. Appl. No. 11/938,832.

Examination report dated Jul. 24, 2009 for U.S. Appl. No. 11/975,896.

Examination report dated Jul. 27, 2009 for U.S. Appl. No. 12/102,662.

Examination report dated Jul. 29, 2009 for U.S. Appl. No. 11/807,887.

Examination report dated Jul. 30, 2009 for U.S. Appl. No. 11/807,837.

Examination report dated Aug. 10, 2009 for U.S. Appl. No. 12/017,855.

Examination report dated Aug. 13, 2009 for U.S. Appl. No. 11/807,681.

Examination report dated Oct. 15, 2009 for U.S. Appl. No. 12/313,298.

Examination report dated Oct. 16, 2009 for U.S. Appl. No. 12/102,953.

Examination report dated Nov. 10, 2009 for U.S. Appl. No. 12/172,645.

Examination report dated Nov. 19, 2009 for U.S. Appl. No. 11/938,846.

Examination report dated Nov. 30, 2009 for U.S. Appl. No. 12/220,362.

Examination report dated Dec. 10, 2009 for U.S. Appl. No. 12/229,187.

Examination report dated Dec. 14, 2009 for U.S. Appl. No. 12/229,203.

Examination report dated Jan. 13, 2010 for U.S. Appl. No. 12/017,827.

Examination report dated Jan. 14, 2010 for U.S. Appl. No. 11/807,887.

Examination report dated Jan. 14, 2010 for U.S. Appl. No. 12/114,090.

Examination report dated Feb. 19, 2010 for U.S. Appl. No. 12/055,014.

Examination report dated Feb. 25, 2010 for U.S. Appl. No. 11/938,832.
Examination report dated Mar. 11, 2010 for U.S. Appl. No. 12/102,983.
Examination report dated Apr. 5, 2010 for U.S. Appl. No. 12/017,886.
Examination report dated Apr. 12, 2010 for U.S. Appl. No. 11/938,846.
Examination report dated Apr. 21, 2010 for U.S. Appl. No. 11/807,887.
Examination report dated May 3, 2010 for U.S. Appl. No. 12/356,980.
Examination report dated May 3, 2010 for U.S. Appl. No. 12/357,031.
Examination report dated May 4, 2010 for U.S. Appl. No. 11/807,681.
Examination report dated May 6, 2010 for U.S. Appl. No. 11/364,013.
Examination report dated May 24, 2010 for U.S. Appl. No. 12/217,279.
Examination report dated May 28, 2010 for U.S. Appl. No. 11/938,841.
Examination report dated Jun. 24, 2010 for U.S. Appl. No. 12/017,855.
Examination report dated Jul. 21, 2010 for U.S. Appl. No. 12/229,187.
Examination report dated Jul. 23, 2010 for U.S. Appl. No. 12/229,203.
Examination report dated Jul. 29, 2010 for U.S. Appl. No. 12/378,332.
Examination report dated Aug. 25, 2010 for U.S. Appl. No. 12/313,298.
International Search Report dated May 7, 2008 for PCT/CA08/000449.
International Preliminary Examination Report dated Sep. 15, 2009 for PCT/CA08/000449.
Examination report dated Jan. 28, 2011 for corresponding application EP 08 733 553.5.
Examination report dated Jan. 6, 2011 for U.S. Appl. No. 11/807,887.

* cited by examiner

FIGURE 1

| Diagnosis | | Total | - | +/- | + | ++ | +++ | Total Positive | % of Positive |
|---|---|---|---|---|---|---|---|---|---|
| H460-16-2 | | | | | | | | | |
| Tumor | | 49 | 28 | 7 | 8 | 3 | 3 | 21 | 43% |
| Primary Hepatocellular Carcinoma | | 37 | 26 | 4 | 5 | 1 | 1 | 11 | 30% |
| Metastatic Hepatocellular Carcinoma | | 8 | 1 | 3 | 3 | 1 | 0 | 7 | 88% |
| Primary Cholangiocarcinoma | | 2 | 1 | 0 | 0 | 0 | 1 | 1 | 50% |
| Metastatic Cholangiocarcinoma | | 2 | 0 | 0 | 0 | 1 | 1 | 2 | 100% |
| Tumor Stages (AJCC) | I | 2 | 2 | 0 | 0 | 0 | 0 | 0 | 0% |
| | II | 17 | 15 | 0 | 1 | 1 | 0 | 2 | 12% |
| | III | 16 | 8 | 4 | 3 | 0 | 1 | 8 | 50% |
| | IV | 8 | 2 | 2 | 3 | 0 | 1 | 6 | 75% |
| Normal | | 9 | 0 | 0 | 1 | 3 | 5 | 9 | 100% |

Figure 7

| Frequency of Metastases Occurrence in Treated vs. Untreated Animals | | | | |
|---|---|---|---|---|
| | Lung metastases | Intrahepatic metastases | Intestine metastases | Urinary metastases |
| Control | 5/5=100% | 5/5=100% | 4/5=80% | 3/5=60% |
| 2 mg/kg | 0/5=0% | 2/5=40% | 1/5=20% | 1/5=20% |
| 10 mg/kg | 0/5=0% | 1/5=20% | 0/5=0% | 0/5=0% |
| 20 mg/kg | 0/5=0% | 0/5=0% | 0/5=0% | 0/5=0% |

CYTOTOXICITY MEDIATION OF CELLS EVIDENCING SURFACE EXPRESSION OF CD44

REFERENCE TO RELATED APPLICATIONS

This application is a continuation-in-part to U.S. patent application Ser. No. 11/716,216, filed on Mar. 9, 2007, now abandoned, which is a continuation-in-part to U.S. patent application Ser. No. 11/364,013, filed on Feb. 28, 2006, which is now allowed (U.S. Pat. No. 7,947,496), which is a continuation-in-part to U.S. patent application Ser. No. 10/810,165, filed Mar. 26, 2004, now abandoned, which is a continuation-in-part to U.S. patent application Ser. No. 10/647,818, filed Aug. 22, 2003, now U.S. Pat. No. 7,189,397, issued Mar. 13, 2007, which is a continuation-in-part to U.S. patent application Ser. No. 10/603,000, filed Jun. 23, 2003, now U.S. Pat. No. 7,252,821, issued Aug. 7, 2007, which is a continuation-in-part to U.S. patent application Ser. No. 09/727,361 filed Nov. 29, 2000 now U.S. Pat. No. 6,657,048, issued Dec. 2, 2003, which is a continuation-in-part to U.S. patent application Ser. No. 09/415,278 filed Oct. 8, 1999, now U.S. Pat. No. 6,180,357, issued Jan. 30, 2001, the contents of each of which are herein incorporated by reference.

FIELD OF THE INVENTION

This invention relates to the isolation and production of cancerous disease modifying antibodies (CDMAB) and to the use of these CDMAB alone or in combination with one or more CDMAB/chemotherapeutic agents in therapeutic and diagnostic processes. The invention further relates to binding assays which utilize the CDMAB of the instant invention.

BACKGROUND OF THE INVENTION

CD44 in Cancer: Raising monoclonal antibodies against human white blood cells led to the discovery of the CD44 antigen; a single chain hyaluronic acid (HA) binding glycoprotein expressed on a wide variety of normal tissue and on all types of hematopoietic cells. It was originally associated with lymphocyte activation and homing. Currently, its putative physiological role also includes activation of inflammatory genes, modulation of cell cycle, induction of cell proliferation, induction of differentiation and development, induction of cytoskeletal reorganization and cell migration and cell survival/resistance to apoptosis.

In humans, the single gene copy of CD44 is located on the short arm of chromosome 11, 11p13. The gene contains 19 exons; the first 5 are constant, the next 9 are variant, the following 3 are constant and the final 2 are variant. Differential splicing can lead to over 1000 different isoforms. However, currently only several dozen naturally occurring variants have been identified.

The CD44 standard glycoprotein consists of a N-terminal extracellular (including a 20 a.a. leader sequence, and a membrane proximal region (85 a.a.)) domain (270 a.a.), a transmembrane region (21 a.a.) and a cytoplasmic tail (72 a.a.). The extracellular region also contains a link module at the N-terminus. This region is 92 a.a. in length and shows homology to other HA binding link proteins. There is high homology between the mouse and human forms of CD44. The variant forms of the protein are inserted to the carboxy terminus of exon 5 and are located extracellularly when expressed.

A serum soluble form of CD44 also occurs naturally and can arise from either a stop codon (within the variable region) or from proteolytic activity. Activation of cells from a variety of stimuli including TNF-α results in shedding of the CD44 receptor. Shedding of the receptor has also been seen with tumor cells and can result in an increase in the human serum concentration of CD44 by up to 10-fold. High CD44 serum concentration suggests malignancy (ovarian cancer being the exception).

The standard form of CD44 exists with a molecular weight of approximately 37 kD. Post-translational modifications increase the molecular weight to 80-90 kD. These modifications include amino terminus extracellular domain N-linked glycosylations at asparagine residues, O-linked glycosylations at serine/threonine residues at the carboxy terminus of the extracellular domain and glycosaminoglycan additions. Splice variants can range in size from 80-250 kD.

HA, a polysaccharide located on the extracellular matrix (ECM) in mammals, is thought to be the primary CD44 ligand. However, CD44 has also been found to bind such proteins as collagen, fibronectin, laminin etc. There appears to be a correlation between HA binding and glycosylation. Inactive CD44 (does not bind HA) has the highest levels of glycosylation, active CD44 (binding HA) the lowest while inducible CD44 (does not or weakly binds HA unless activated by cytokines, monoclonal antibodies, growth factors, etc.) has glycosylation levels somewhere in between the active and inactive forms.

CD44 can mediate some of its functions through signal transduction pathways that depend on the interaction of the cell, stimulus and the environment. Some of these pathways include the NFκB signaling cascade (involved in the inflammatory response), the Ras-MAPK signal transduction pathway (involved with activating cell cycling and proliferation), the Rho family of proteins (involved with cytoskeleton reorganization and cell migration) and the PI3-K-related signaling pathway (related to cell survival). All of the above-mentioned functions are closely associated with tumor disease initiation and progression. CD44 has also been implicated in playing a role in cancer through a variety of additional mechanisms. These include the presentation of growth factors, chemokines and cytokines by cell surface proteoglycans present on the cell surface of CD44 to receptors involved in malignancy. Also, the intracellular degradation of HA by lysosomal hyaluronidases after internalization of the CD44-HA complex can potentially increase the likelihood of tumor invasiveness and induction of angiogenesis through the ECM. In addition, the transmission of survival or apoptotic signals has been shown to occur through either the standard or variable CD44 receptor. CD44 has also been suggested to be involved in cell differentiation and migration. Many, if not all, of these mechanisms are environment and cell dependent and several give rise to variable findings. Therefore, more research is required before any conclusions can be drawn.

In order to validate a potential functional role of CD44 in cancer, expression studies of CD44 were undertaken to determine if differential expression of the receptor correlates with disease progression. However, inconsistent findings were observed in a majority of tumor types and this is probably due to a combination of reagents, technique, pathological scoring and cell type differences between researchers. Renal cell carcinoma and non-Hodgkin's lymphoma appear to be the exception in that patients with high CD44 expressing tumors consistently had shorter survival times than their low or non-CD44 expressing counterparts.

Due to its association with cancer, CD44 has been the target of the development of anti-cancer therapeutics. There is still controversy as to whether the standard or the variant forms of CD44 are required for tumor progression. There is in vivo animal data to support both views and again it may be tumor type and even cell type dependent. Different therapeutic approaches have included injection of soluble CD44 proteins, hyaluronan synthase cDNA, hyaluronidase, the use of CD44 antisense and CD44 specific antibodies. Each approach has led to some degree of success thereby providing support for anti-CD44 cancer therapeutics.

Both variant and standard CD44 specific monoclonal antibodies have been generated experimentally but for the most part these antibodies have no intrinsic biological activity, rather they bind specifically to the type of CD44 they recognize. However, there are some that are either active in vitro or in vivo but generally not both. Several anti-CD44 antibodies have been shown to mediate cellular events. For example the murine antibody A3D8, directed against human erythrocyte Lutheran antigen CD44 standard form, was shown to enhance CD2 (9-1 antibody) and CD3 (OKT3 antibody) mediated T cell activation; another anti-CD44 antibody had similar effects. A3D8 also induced IL-1 release from monocytes and IL-2 release from T lymphocytes. Interestingly, the use of A3D8 in conjunction with drugs such as daunorubicin, mitoxantrone and etoposide inhibited apoptosis induction in HL60 and NB4 AML cells by abrogating the generation of the second messenger ceramide. The J173 antibody, which does not have intrinsic activity and is directed against a similar epitope of CD44s, did not inhibit drug-induced apoptosis. The NIH44-1 antibody, directed against an 85-110 kD and 200 kD form of CD44, augmented T-cell proliferation through a pathway the authors speculated as either cross-linking or aggregation of CD44. Taken together, there is no evidence that antibodies such as these are suitable for use as cancer therapeutics since they either are not directed against cancer (e.g. activate lymphocytes), induce cell proliferation, or when used with cytotoxic agents inhibited drug-induced death of cancer cells.

Several anti-CD44 antibodies have been described which demonstrate anti-tumor effects in vivo. The antibody 1.1ASML, a mouse IgG1 directed to the v6 variant of CD44, has been shown to decrease the lymph node and lung metastases of the rat pancreatic adenocarcinoma BSp73ASML. Survival of the treated animals was concomitantly increased. The antibody was only effective if administered before lymph node colonization, and was postulated to interfere with cell proliferation in the lymph node. There was no direct cytotoxicity of the antibody on the tumor cells in vitro, and the antibody did not enhance complement-mediated cytotoxicity, or immune effector cell function. Utility of the antibody against human cells was not described.

Breyer et al. described the use of a commercially-available antibody to CD44s to disrupt the progression of an orthotopically-implanted rat glioblastoma. The rat glioblastoma cell line C6 was implanted in the frontal lobe, and after 1 week, the rats were given 3 treatments with antibody by intracerebral injection. Treated rats demonstrated decreased tumor growth, and higher body weight than buffer or isotype control treated rats. The antibody was able to inhibit adhesion of cells in vitro to coverslips coated with extracellular matrix components, but did not have any direct cytotoxic effects on cells. This antibody was not tested against human cells.

A study was carried out which compared the efficacy of an antibody to CD44s (IM-7.8.1) to an antibody to CD44v10 (K926). The highly metastatic murine melanoma line B16F 10, which expresses both CD44 isoforms, was implanted intravenously into mice. After 2 days, antibodies were given every third day for the duration of the study. Both antibodies caused a significant reduction of greater than 50 percent in the number of lung metastases; there was no significant difference in efficacy between the two antibodies. The antibody did not affect proliferation in vitro, and the authors, Zawadzki et al., speculated that the inhibition of tumor growth was due to the antibody blocking the interaction of CD44 with its ligand. In another study using IM-7.8.1, Zahalka et al. demonstrated that the antibody and its F(ab')$_2$ fragment were able to block the lymph node infiltration by the murine T-cell lymphoma LB. This conferred a significant survival benefit to the mice. Wallach-Dayan et al. showed that transfection of LB-TRs murine lymphoma, which does not spontaneously form tumors, with CD44v-4-v10 conferred the ability to form tumors. IM-7.8.1 administration decreased tumor size of the implanted transfected cells in comparison to the isotype control antibody. None of these studies demonstrated human utility for this antibody.

GKW.A3, a mouse IgG2a, is specific for human CD44 and prevents the formation and metastases of a human melanoma xenograft in SCID mice. The antibody was mixed with the metastastic human cell line SMMU-2, and then injected subcutaneously. Treatments were continued for the following 3 weeks. After 4 weeks, only 1 of 10 mice developed a tumor at the injection site, compared to 100 percent of untreated animals. F(ab')$_2$ fragments of the antibody demonstrated the same inhibition of tumor formation, suggesting that the mechanism of action was not dependent on complement or antibody-dependent cellular cytotoxicity. If the tumor cells were injected one week prior to the first antibody injection, 80 percent of the animals developed tumors at the primary site. However, it was noted that the survival time was still significantly increased. Although the delayed antibody administration had no effect on the primary tumor formation, it completely prevented the metastases to the lung, kidney, adrenal gland, liver and peritoneum that were present in the untreated animals. This antibody does not have any direct cytotoxicity on the cell line in vitro nor does it interfere with proliferation of SMMU-2 cells, and appears to have its major effect on tumor formation by affecting metastasis or growth. One notable feature of this antibody was that it recognized all isoforms of CD44, which suggests limited possibilities for therapeutic use.

Strobel et al. describe the use of an anti-CD44 antibody (clone 515) to inhibit the peritoneal implantation of human ovarian cancer cells in a mouse xenograft model. The human ovarian cell line 36M2 was implanted intraperitoneally into mice in the presence of the anti-CD44 antibody or control antibody, and then treatments were administered over the next 20 days. After 5 weeks, there were significantly fewer nodules in the peritoneal cavity in the antibody treated group. The nodules from both the anti-CD44 and control treated groups were the same size, suggesting that once the cells had implanted, the antibody had no effect on tumor growth. When cells were implanted subcutaneously there was also no effect on tumor growth indicating that the antibody itself did not have an anti-proliferative or cytotoxic effect. In addition, there was no effect of the antibody on cell growth in vitro.

VFF-18, also designated as BIWA 1, is a high-affinity antibody to the v6 variant of CD44 specific for the 360-370 region of the polypeptide. This antibody has been used as a $^{99m}$Technetium-labelled conjugate in a Phase 1 clinical trial in 12 patients. The antibody was tested for safety and targeting potential in patients with squamous cell carcinoma of the head and neck. Forty hours after injection, 14 percent of the injected dose was taken up by the tumor, with minimal accumulation in other organs including the kidney, spleen and bone marrow. The highly selective tumor binding suggests a role for this antibody in radioimmunotherapy, although the exceptionally high affinity of this antibody prevented penetration into the deeper layers of the tumor. Further limiting the application of BIWA 1 is the immunogenicity of the murine antibody (11 of 12 patients developed human anti-mouse antibodies (HAMA)), heterogenous accumulation throughout the tumor and formation of antibody-soluble CD44 complexes. WO 02/094879 discloses a humanized version of VFF-18 designed to overcome the HAMA response, designated BIWA 4. BIWA 4 was found to have a significantly lower antigen binding affinity than the parent VFF 18 antibody. Surprisingly, the lower affinity BIWA 4 antibody had superior tumor uptake characteristics than the higher affinity BIWA 8 humanized VFF-18 antibody. Both $^{99m}$Technetium-labelled and $^{186}$Rhenium-labelled BIWA 4 antibodies were assessed in a 33 patient Phase 1 clinical trial to determine safety, tolerability, tumor accumulation and maximum tolerated dose, in the case of $^{186}$Re-labelled BIWA 4. There appeared to be tumor related uptake of $^{99m}$Tc-labelled BIWA 4. There were no tumor responses seen with all doses of $^{186}$Re-labelled BIWA 4, although a number had stable disease; the dose limiting toxicity occurred at 60 mCi/m$^2$. There was a 50-65 percent rate of adverse events with 12 of 33 patients deemed to have serious adverse events (thrombocytopenia, leucopenia and fever) and of those 6, all treated with $^{186}$Re-labelled BIWA 4, died in the course of treatment or follow-up due to disease progression. Two patients developed human anti-human antibodies (HAHA). A Phase 1 dose escalation trial of $^{186}$Re-labelled BIWA 4 was carried out in 20 patients. Oral mucositis and dose-limiting thrombocytopenia and leucocytopenia were observed; one patient developed a HAHA response. Stable disease was seen in 5 patients treated at the highest dose of 60 mCi/m$^2$. Although deemed to be acceptable in both safety and tolerablility for the efficacy achieved, these studies have higher rates of adverse events compared to other non-radioisotope conjugated biological therapies in clinical studies. U.S. Patent Application US 2003/0103985 discloses a humanized version of VFF-18 conjugated to a maytansinoid, designated BIWI 1, for use in tumor therapy. A humanized VFF 18 antibody, BIWA 4, when conjugated to a toxin, i.e. BIWI 1, was found to have significant anti-tumor effects in mouse models of human epidermoid carcinoma of the vulva, squamous cell carcinoma of the pharynx or breast carcinoma. The unconjugated version, BIWA 4, did not have anti-tumor effects and the conjugated version, BIWI 1, has no evidence of safety or efficacy in humans.

Mab U36 is a murine monoclonal IgG1 antibody generated by UM-SCC-22B human hypopharyngeal carcinoma cell immunization and selection for cancer and tissue specificity. Antigen characterization through cDNA cloning and sequence analysis identified the v6 domain of keratinocyte-specific CD44 splice variant epican as the target of Mab U36. Immunohistochemistry studies show the epitope to be restricted to the cell membrane. Furthermore, Mab U36 labeled 94 percent of the head and neck squamous cell carcinomas (HNSCC) strongly, and within these tumors there was uniformity in cell staining. A 10 patient $^{99m}$Tc-labelled Mab U36 study showed selective accumulation of the antibody to HNSCC cancers (20.4+/−12.4 percent injected dose/kg at 2 days); no adverse effects were reported but two patients developed HAMA. In a study of radio-iodinated murine Mab U36 there were 3 cases of HAMA in 18 patients and selective homogenous uptake in HNSCC. In order to decrease the antigenicity of Mab U36 and decrease the rate of HAMA a chimeric antibody was constructed. Neither the chimeric nor the original murine Mab U36 has ADCC activity. There is no evidence of native functional activity of Mab U36. $^{186}$Re-labelled chimeric Mab U36 was used to determine the utility of Mab U36 as a therapeutic agent. In this Phase 1 escalating dose trial 13 patients received a scouting dose of $^{99m}$Tc-labelled chimeric Mab U36 followed by $^{186}$Re-labelled chimeric Mab U36. There were no acute adverse events reported but following treatment dose limiting myelotoxcity (1.5 GBq/m$^2$) in 2 of 3 patients, and thrombocytopenia in one patient treated with the maximum tolerated dose (1.0 GBq/m$^2$) were observed. Although there were some effects on tumor size these effects did not fulfill the criteria for objective responses to treatment. A further study of $^{186}$Re-labelled chimeric Mab U36 employed a strategy of using granulocyte colony-stimulating factor stimulated whole blood reinfusion to double the maximum-tolerated activity to 2.8 Gy. In this study of nine patients with various tumors of the head and neck, 3 required transfusions for drug related anemia. Other toxicity includes grade 3 myelotoxicity, and grade 2 mucositis. No objective tumor responses were reported although stable disease was achieved for 3-5 months in 5 patients. Thus, it can be seen that although Mab U36 is a highly specific antibody the disadvantage of requiring a radioimmunoconjugate to achieve anticancer effects limits its usefulness because of the toxicity associated with the therapy in relation to the clinical effects achieved.

To summarize, a CD44v6 (1.1ASML) and CD44v10 (K926) monoclonal antibody have been shown to reduce metastatic activity in rats injected with a metastatic pancreatic adenocarcinoma or mice injected with a malignant melanoma respectively. Another anti-CD44v6 antibody (VFF-18 and its derivatives), only when conjugated to a maytansinoid or a radioisotope, has been shown to have anti-tumor effects. Anti-standard CD44 monoclonal antibodies have also been shown to suppress intracerebral progression by rat glioblastoma (anti-CD44s), lymph node invasion by mouse T cell lymphoma (IM-7.8.1) as well as inhibit implantation of a human ovarian cancer cell line in nude mice (clone 515), lung metastasis of a mouse melanoma cell line (IM-7.8.1) and metastasis of a human melanoma cell line in SCID mice (GKW.A3). The radioisotope conjugated Mab U36 anti-CD44v6 antibody and its derivatives had anti-tumor activity in clinical trials that were accompanied by significant toxicity. These results, though they are encouraging and support the development of anti-CD44 monoclonal antibodies as potential cancer therapeutics, demonstrate limited effectiveness, safety, or applicability to human cancers.

Thus, if an antibody composition were isolated which mediated cancerous cell cytotoxicity, as a function of its attraction to cell surface expression of CD44 on said cells, a valuable diagnostic and therapeutic procedure would be realized.

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (Herceptin®) in combination with CISPLATIN. In this trial 37 patients were assessed for responses of which about a quarter had a partial response rate and an additional quarter had minor or stable disease progression. The median time to progression among the responders was 8.4 months with median response duration of 5.3 months.

Herceptin® was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin® plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin® and Taxol® led to a higher incidence of cardiotoxicity in comparison to Taxol® treatment alone (13 versus 1 percent respectively). Also, Herceptin® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like Herceptin®, treatment in Switzerland is only approved as a combination of monoclonal antibody and chemotherapy. In addition, treatment in both Switzerland and the US is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like Herceptin® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXOTERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that could contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including Herceptin® and RITUXIMAB, have been produced using these methods and selected on the basis of their affinity. The flaws in this strategy are two-fold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, have been inadequate for all types of cancer.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single-chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies, which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is 2-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,916,561 discloses a specific antibody, VFF-18, and its variants directed against the variant exon v6 of the CD44 gene. This antibody is an improvement over the comparator antibody in that it recognizes a human CD44 v6 variant rather than a rat CD44 v6 variant. In addition this antibody discloses diagnostic assays for CD44 v6 expression. There was no in vitro or in vivo function disclosed for this antibody.

U.S. Pat. No. 5,616,468 discloses a monoclonal antibody, Var3.1, raised against a synthetic peptide containing a sequence encoded by the human exon 6A of the CD44 gene. Specifically this antibody does not bind to the 90 kD form of human CD44 and is distinguished from the Hermes-3 antibody. A method for detection of the v6 variant of CD44 is provided, as well as a method for screening and assaying for malignant transformation based on this antigen. A method for screening for inflammatory disease based on detecting the antigen in serum is also provided.

U.S. Pat. No. 5,879,898 discloses a specific antibody that binds to a 129 bp exon of a human CD44 variant 6 that produces a 43 amino acid peptide. The monoclonal antibody is produced by a number of hybridoma cell lines: MAK<CD44>M-1.1.12, MAK<CD44>M-2.42.3, MAK<CD44>M-4.3.16. The antibody is generated from a fusion protein that contains at least a hexapeptide of the novel CD44 v6 amino acid sequence. Further, there is a disclosure of an immunoassay for the detection of exon 6 variant that can be used as a cancer diagnostic. Significantly, there is no in vitro or in vivo function of this antibody disclosed.

U.S. Pat. No. 5,942,417 discloses a polynucleotide that encodes a CD44 like polypeptide, and the method of making a recombinant protein using the polynucleotide and its variants. Antibodies are claimed to these polypeptides however there are no specific examples and there are no deposited clones secreting such antibodies. Northern blots demonstrate the appearance of the polynucleotide in several types of tissues, but there is no accompanying evidence that there is translation and expression of this polynucleotide. Therefore, there is no evidence that there were antibodies to be made to the gene product of this polynucleotide, that these antibodies would have either in vitro or in vivo function, and whether they would be relevant to human cancerous disease.

U.S. Pat. No. 5,885,575 discloses an antibody that reacts with a variant epitope of CD44 and methods of identifying the variant through the use of the antibody. The isolated polynucleotide encoding this variant was isolated from rat cells, and the antibody, mAb1.ASML, directed against this variant recognizes proteins of molecular weight 120 kD, 150 kD, 180 kD, and 200 kD. The administration of monoclonal antibody 1.1ASML delayed the growth and metastases of rat BSp73ASML in isogenic rats. Significantly 1.1ASML does not recognize human tumors as demonstrated by its lack of reactivity to LCLC97 human large-cell lung carcinoma. A human homolog was isolated from LCLC97 but no equivalent antibody recognizing this homolog was produced. Thus, although an antibody specific to a variant of rat CD44 was produced and shown to affect the growth and metastasis of rat tumors there is no evidence for the effect the this antibody against human tumors. More specifically the inventors point out that this antibody does not recognize human cancers.

SUMMARY OF THE INVENTION

This application utilizes methodology for producing patient specific anti-cancer antibodies taught in the U.S. Pat. No. 6,180,357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinities of these antibodies are suited to requirements for initiation of the cytotoxic events that may not be amenable to stronger affinity interactions. Also, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, cytokines, interferons, target or reporter moieties or hematogenous cells, thereby forming an antibody conjugate. The CDMAB can be used alone or in combination with one or more CDMAB/chemotherapeutic agents.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity (ADCC) or complement dependent cytotoxicity (CDC). For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

The cytotoxicity mediated through the Fc region requires the presence of effector cells, their corresponding receptors, or proteins e.g. NK cells, T cells and complement. In the absence of these effector mechanisms, the Fc portion of an antibody is inert. The Fc portion of an antibody may confer properties that affect the pharmacokinetics of an antibody in vivo, but in vitro this is not operative.

The cytotoxicity assays under which we test the antibodies do not have any of the effector mechanisms present, and are carried out in vitro. These assays do not have effector cells (NK, Macrophages, or T-cells) or complement present. Since these assays are completely defined by what is added together, each component can be characterized. The assays used herein contain only target cells, media and sera. The target cells do not have effector functions since they are cancer cells or fibroblasts. Without exogenous cells which have effector function properties there is no cellular elements that have this function. The media does not contain complement or any cells. The sera used to support the growth of the target cells do not have complement activity as disclosed by the vendors. Furthermore, in our own labs we have verified the absence of complement activity in the sera used. Therefore, our work evidences the fact that the effects of the antibodies are due entirely to the effects of the antigen binding which is mediated through the Fab. Effectively, the target cells are seeing and interacting with only the Fab, since they do not have receptors for the Fc. Although the hybridoma is secreting complete immunoglobulin which was tested with the target cells, the only part of the immunoglobulin that interacts with the cells are the Fab, which act as antigen binding fragments.

With respect to the instantly claimed antibodies and antigen binding fragments, the application, as filed, has demonstrated cellular cytotoxicity as evidenced by the data in FIG. 1. As pointed out above, and as herein confirmed via objective evidence, this effect was entirely due to binding by the Fab to the tumor cells.

Ample evidence exists in the art of antibodies mediating cytotoxicity due to direct binding of the antibody to the target antigen independent of effector mechanisms recruited by the Fc. The best evidence for this is in vitro experiments which do not have supplemental cells, or complement (to formally exclude those mechanisms). These types of experiments have been carried out with complete immunoglobulin, or with antigen binding fragments such as F(ab)'2 fragments. In these types of experiments, antibodies or antigen binding fragments can directly induce apoptosis of target cells such as in the case of anti-Her2 and anti-EGFR antibodies, both of which have been approved by the US FDA for marketing in cancer therapy.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematology 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end 2003, there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Using substantially the process of U.S. Pat. No. 6,180,357, the mouse monoclonal antibody H460-16-2 was obtained following immunization of mice with cells from a patient's lung tumor biopsy and from the lung cancer cell line NCI-H460 (ATCC, Virginia, Mass.). The H460-16-2 antigen was expressed on the cell surface of a broad range of human cell lines from different tissue origins. The breast cancer cell line MDA-MB-231 (MB-231) and skin cancer cell line A2058 were susceptible to the cytotoxic effects of H460-16-2 in vitro.

The result of H460-16-2 cytotoxicity against MB-231 cells in culture was further extended by its anti-tumor activity towards these cancer cells when transplanted into mice (as disclosed in Ser. No. 10/603,000). Pre-clinical xenograft tumor models are considered valid predictors of therapeutic efficacy.

In the preventative in vivo model of human breast cancer, H460-16-2 treatment was significantly (p<0.0001) more effective in suppressing tumor growth during the treatment period than an isotype control antibody. At the end of the treatment phase, mice given H460-16-2 had tumors that grew to only 1.3 percent of the control group. During the post treatment follow-up period, the treatment effects of H460-16-2 were sustained and the mean tumor volume in the treated groups continued to be significantly smaller than controls until the end of the measurement phase. Using survival as a measure of antibody efficacy, it was estimated that the risk of dying in the H460-16-2 treatment group was about 71 percent of the antibody buffer control group (p=0.028) at 70 days post-treatment. These data demonstrated that H40-16-2 treatment conferred a survival benefit compared to the control-treated groups. H460-16-2 treatment appeared safe, as it did not induce any signs of toxicity, including reduced body weight and clinical distress. Thus, H460-16-2 treatment was efficacious as it both delayed tumor growth and enhanced survival compared to the control-treated groups in a well-established model of human breast cancer.

In addition, H460-16-2 demonstrated anti-tumor activity against MB-231 cells in an established in vivo tumor model (as disclosed in Ser. No. 10/603,000). Treatment with H460-16-2 was compared to the standard chemotherapeutic drug, Cisplatin, and it was shown that the Cisplatin and H460-16-2 treatment groups had significantly (p<0.001) smaller mean tumor volumes compared with groups treated with either antibody dilution buffer or the isotype control antibody. H460-16-2 treatment mediated tumor suppression that was approximately two-thirds that of Cisplatin chemotherapy but without the significant (19.2 percent) weight loss (p<0.003) and clinical distress, including 2 treatment-associated deaths, observed with Cisplatin treatment. The anti-tumor activity of H460-16-2 and its minimal toxicity make it an attractive anti-cancer therapeutic agent.

In the post-treatment period, H460-16-2 showed a significant survival benefit (p<0.02) as the risk of dying in the H460-16-2 group was about half of that in the isotype control antibody group at >70 days after treatment. The observed survival benefit continued past 120 days post-treatment where 100 percent of the isotype control and Cisplatin treated mice had died compared to 67 percent of the H460-16-2 treatment group. H460-16-2 maintained tumor suppression by delaying tumor growth by 26 percent compared to the isotype control antibody group. At 31 days post treatment, H460-16-2 limited tumor size by reducing tumor growth by 48 percent compared to the isotype control group, which is comparable to the 49 percent reduction observed at the end of the treatment. In the established tumor model of breast cancer, these results indicated the potential of H460-16-2 to maintain tumor suppression beyond the treatment phase and demonstrated the ability of the antibody to reduce the tumor burden and enhance survival in a mammal.

In addition to the beneficial effects in the established in vivo tumor model of breast cancer, H460-16-2 treatment in combination with a chemotherapeutic drug (Cisplatin) had anti-tumor activity against PC-3 cells in an established in vivo prostate cancer model (as disclosed in Ser. No. 10/810,165). Using a paired t-test, H460-16-2 plus Cisplatin treatment was significantly more effective in suppressing tumor growth shortly after the treatment period than buffer control (p<0.0001), Cisplatin treatment alone (p=0.004) or H460-16-2 treatment alone (p<0.0001). At the end of the treatment phase, mice given H460-16-2 plus Cisplatin had tumors that grew to only 28.5 percent of the buffer control group. For PC-3 SCID xenograft models, body weight can be used as a surrogate indicator of disease progression. Mice in all the groups experienced severe weight loss. In this study, mice in all groups showed a weight loss of approximately 23 to 35 percent by the end of the treatment period. The group treated with H460-16-2 showed the smallest degree of weight loss (21.7 percent). After treatment, day 48, there was no significant increase in weight loss associated with the treatment of H460-16-2 and Cisplatin in comparison to buffer control (p=0.5042). Thus, H460-16-2 plus Cisplatin treatment was efficacious as it delayed tumor growth compared to the isotype control treated group in a well-established model of human prostate cancer.

In order to validate the H460-16-2 epitope as a drug target, the expression of H460-16-2 antigen in normal human tissues was previously determined (Ser. No. 10/603,000). This work was extended by comparison with the anti-CD44 antibodies; clone L178 (disclosed in Ser. No. 10/647,818) and clone BU75 (disclosed in Ser. No. 10/810,165). By IHC staining with H460-16-2, the majority of the tissues failed to express the H460-16-2 antigen, including the cells of the vital organs, such as the liver, kidney (except for marginal staining of tubular epithelial cells), heart, and lung. Results from tissue staining indicated that H460-16-2 showed restricted binding to various cell types but had binding to infiltrating macrophages, lymphocytes, and fibroblasts. The BU75 antibody showed a similar staining pattern. However, there was at least one difference of note; staining of lymphocytes was more intense with BU75 in comparison to H460-16-2.

Localization of the H460-16-2 antigen and determining its prevalence within the population, such as among breast cancer patients, is important in assessing the therapeutic use of H460-16-2 and designing effective clinical trials. To address H460-16-2 antigen expression in breast tumors from cancer patients, tumor tissue samples from 50 individual breast cancer patients were previously screened for expression of the H460-16-2 antigen (Ser. No. 10/603,000) and was compared to L178 (Ser. No. 10/647,818), BU75 (Ser. No. 10/810,165) and the anti-Her2 antibody c-erbB-2 (Ser. No. 10/810,165). The results of these studies were similar and showed that 62 percent of tissue samples stained positive for the H460-16-2 antigen while 73 percent of breast tumor tissues were positive for the BU75 epitope. Expression of H460-16-2 within patient samples appeared specific for cancer cells as staining was restricted to malignant cells. H460-16-2 stained 4 of 10 samples of normal tissue from breast cancer patients while BU75 stained 8. Breast tumor expression of both the H460-16-2 and BU75 antigen appeared to be mainly localized to the cell membrane of malignant cells, making CD44 an attractive target for therapy. H460-16-2 expression was further evaluated based on breast tumor expression of the receptors for the hormones estrogen and progesterone, which play an important role in the development, treatment, and prognosis of breast tumors. No correlation was apparent between expression of the H460-16-2 antigen and expression of the receptors for either estrogen or progesterone. When tumors were analyzed based on their stage, or degree to which the cancer advanced, again there was no clear correlation between H460-16-2 antigen expression and tumor stage. Similar results were obtained with BU75. In comparison to c-erbB-2, H460-16-2 showed a completely different staining profile where 52 percent of the breast tumor tissue samples that were positive for the H460-16-2 antigen were negative for Her2 expression indicating a yet unmet targeted therapeutic need for breast cancer patients. There were also differences in the intensity of staining between the breast tumor tissue sections that were positive for both H460-16-2 and Her2. The c-erbB-2 antibody also positively stained one of the normal breast tissue sections.

To further extend the potential therapeutic benefit of H460-16-2, the frequency and localization of the antigen within various human cancer tissues was also previously determined (Ser. No. 10/603,000) and was compared to clone L178 (Ser. No. 10/647,818). The majority of these tumor types were also positive for the L178 antigen. As with human breast tumor tissue, H460-16-2 and L178 localization occurred on the membrane of tumor cells. However, there was substantially more membrane localization with the L178 compared to the H460-16-2 antibody. Also, of the tumor types that were stained by both H460-16-2 and L178, 43 percent of the tissues showed higher intensity staining with the L178 antibody.

In addition, the frequency and localization of the antigen within prostate and liver normal and cancer tissues was previously determined (Ser. No. 11/364,013). From the prostate cancer array, 19/53 (36 percent) of the tested tumors were positive for H460-16-2. H460-16-2 was specific for tumor cells and stroma fibroblasts. Cellular localization was mostly membranous and cytoplasmic membranous with or without luminal localization. The percentage of positive cells ranged from <10 percent->50 percent indicating heterogenous binding of the antibody to tumor cells. The relation of the antibody binding to tumors' stages could not be assessed properly due to a discrepancy in the number of tumors among different tumor stages, being 1/1 (100 percent), 4/12 (33 percent), 0/2 (0 percent) and 11/33 (33 percent) to stage I, II, III and IV, respectively. There was higher binding to Gleason score G3-G4 (36 percent) than to G1-G2 (25 percent). The Gleason score is a system of grading prostate cancer. The Gleason grading system assigns a grade to each of the two largest areas of cancer in the tissue samples. Grades range from 1 to 5 with 1 being the least aggressive and 5 the most aggressive. Grade 3 tumors, for example, seldom have metastases, but metastases are common with grade 4 or grade 5. The two grades are then added together to produce a Gleason score. A score of 2 to 4 is considered low grade; 5 through 7, intermediate grade; and 8 through 10, high grade. A tumor with a low Gleason score typically grows slowly enough that it may not pose a significant threat to the patient in his lifetime. All 3 normal prostate tissue sections were positive for the antibody. However, the tissue specificity was for myoepithelium and stromal fibroblasts and spared the glandular epithelium. FIG. 12 demonstrates the heterogeneity of the binding of H460-16-2 to tested prostate tumors: 10/53, 6/53, 3/53 positive tumors were in the categories of <10-10 percent, <50-50 percent and >50 percent, respectively. As a result of its binding to prostate cancer cells, the therapeutic benefit of H460-16-2 can potentially be extended to the treatment of prostate cancer.

From the liver cancer array, H460-16-2 antibody showed binding to 21/49 (43 percent) of tested liver cancers, including 11/37 (30 percent) of primary, 7/8 (88 percent) of metastatic hepatocellular carcinoma, 1/2 (50 percent) of primary and 2/2 (100 percent) of metastatic cholangiocarcinomas. The antibody showed significant higher binding to advanced tumors' stages III and IV in comparison with early stages I and II (p=0.03) [stage I, 0/2 (0 percent); stage II, 2/17 (12 percent); stage III, 8/16 (50 percent) and stage IV, 6/8 (75 percent)]. H460-16-2 was specific for tumor cells and infiltrating inflammatory cells. Cellular localization was mainly membranous. Some tumors also displayed a diffuse cytoplasmic staining pattern. The antibody bound to 9/9 of non-neoplastic liver tissues. However, the binding was restricted to the sinusoidal cells and infiltrating lymphocytes. The H460-16-2 antigen appears to be specifically expressed on advanced liver tumor tissue. H460-16-2 therefore has potential as a therapeutic drug in the treatment of liver cancer.

There appears to be no form of CD44 that exactly matches the IHC data presented herein based on comparisons with the IHC data from the literature. The standard form of CD44 is normally expressed in the human brain; the H460-16-2 antigen is not. Antibodies directed against pan-CD44 isoforms do not stain the liver (including Kuppfer cells) and positively stain the endometrial glands in all phases of the reproductive cycle. The H460-16-2 antigen is clearly present on Kuppfer cells and is only present on the secretory endometrial glands of the reproductive cycle. H460-16-2 antigen is clearly present on tissue macrophages and only the variant forms V4/5 and V8/9 show occasional macrophage staining. The similar yet distinct binding pattern seen with H460-16-2 in comparison to anti-CD44 L178 and now BU75 indicates that the H460-16-2 antigen is an unique epitope of CD44.

As disclosed previously (Ser. No. 10/647,818), additional biochemical data also indicated that the antigen recognized by H460-16-2 is one of the forms of CD44. This was supported by studies that showed a monoclonal antibody (L178) reactive against CD44 identifies proteins that were bound to H460-16-2 by immunoprecipitation. Western blotting studies also suggested that the epitope of CD44 recognized by H460-16-2 was not present on v6 or v10. The H460-16-2 epitope was also distinguished by being carbohydrate and conformation dependent, whereas many anti-CD44 antibodies are directed against peptide portions of CD44. These IHC and biochemical results demonstrated that H460-16-2 binds to a variant of the CD44 antigen. Thus, the preponderance of evidence showed that H460-16-2 mediates anti-cancer effects through ligation of an unique carbohydrate dependent conformational epitope present on a variant of CD44. For the purpose of this invention, said epitope is defined as a "CD44 antigenic moiety" characterized by its ability to bind with a monoclonal antibody encoded by the hybridoma cell line H460-16-2, antigenic binding fragments thereof or antibody conjugates thereof.

In order to further elucidate the mechanism behind H460-16-2's anti-cancer effects, hyaluronic acid (HA) binding assays were performed (as disclosed in Ser. No. 10/810,165). It was determined that an average concentration of 1.87 (+/− 1.01) micrograms/mL of H460-16-2 was required to inhibit adhesion of MDA-MB-231 cells to HA by 50 percent. These results indicated that H460-16-2 interacts with, at least in part, the region(s) on CD44 that are responsible for binding to HA and consequently could be mediating its anti-cancer effects through down regulation of angiogenesis or tumor invasiveness through the ECM.

In addition to the HA binding assays, a cell cycling experiment was performed in order to determine if the H460-16-2 in vitro and in vivo anti-cancer effects were due to regulation of the cell cycle (as disclosed in Ser. No. 10/810,165). After 24 hours and with 20 micrograms/mL of H460-16-2, there was an increase in the number of MDA-MB-231 apoptotic cells in comparison to the isotype control. This effect also appeared to be dose dependent. Therefore, the efficacy of H460-16-2 might be also due, in whole or in part, to its apoptotic inducing capabilities.

To further elucidate the mechanism of action for H460-16-2, the effect of H460-16-2 treatment upon apoptosis in MDA-MB-231 tumors grown in vivo in a xenograft model of breast cancer was investigated (as disclosed in Ser. No. 11/364,013). Apoptotic cells were counted using morphological criteria such as deletion of single cells, cell shrinkage and compaction of chromatin into a dense mass. The buffer control treatment group yielded an average total score of 17 cells (±5.29) while the H460-16-2 treated group yielded an average total score of 22.5 cells (±4.20). Therefore, there is a trend towards increased apoptosis with H460-16-2 treatment as determined using cellular morphology.

Two chimeric versions of H460-16-2 were generated as disclosed in Ser. No. 11/364,013. One version is of isotype IgG1, kappa ((ch)ARH460-16-2-IgG1) and the other is of isotype IgG2, kappa ((ch)ARH460-16-2-IgG2). Supernatants from chimeric IgG1 and chimeric IgG2-secreting clones were able to detect CD44 in a Western blot, with a signal that was similar to that obtained with the murine H460-16-2 (as disclosed in Ser. No. 11/364,013).

Both of the chimeric antibodies were compared to the murine version of H460-16-2 in an established model of breast cancer (as disclosed in Ser. No. 11/364,013). Both murine H460-16-2 and (ch)ARH460-16-2-IgG1 reduced tumor growth in an established MDA-MB-231 in vivo model of human breast cancer. At day 62, 5 days after the last dose was administered, treatment with H460-16-2 resulted in a tumor growth inhibition of 39 percent (Mean T/C=57 percent). This reduction in tumor growth was significantly different from the control (p=0.0037). The chimeric antibody (ch)ARH460-16-2-IgG1 resulted in an enhanced tumor growth inhibition (TGI) of 64 percent (Mean T/C=26.9 percent; p<0.0001). By contrast, the IgG2 version of the chimeric antibody, (ch)ARH460-16-2-IgG2 showed no inhibition in tumor growth when compared with the buffer control (TGI=0 percent; Mean T/C=122 percent; p=0.7264).

Annexin-V staining was performed to determine whether the chimeric versions of H460-16-2 were able to induce apoptosis in the same manner as the murine counterpart on the MDA-MB-231 human breast cancer cell line (as disclosed in Ser. No. 11/364,013). Spontaneous apoptotic effects of cells treated with isotype control were found to be similar to cells treated with vehicle only. The murine and human chimeric IgG1 and IgG2H460-16-2 antibodies were all found to induce apoptosis in the breast cancer cell line in a dose dependent manner in each experiment, with greater apoptotic effect seen with both the (ch)ARH460-16-2 IgG1 and IgG2 antibodies. Results indicate that in vitro the (ch)ARH460-16-2-IgG2 antibody has the greatest apoptotic effect when compared to the chimeric IgG1 antibody. All 3 antibodies showed an increase in the percentage necrotic and necrotic/apoptotic populations over their prospective isotype controls. The largest increase in the percentage necrotic and necrotic/apoptotic populations was seen with (ch)ARH460-16-2-IgG2, then (ch)ARH460-16-2-IgG 1 and then H460-16-2.

In toto, this data demonstrates that the murine and chimeric H460-16-2 antigen is a cancer associated antigen and is expressed in humans, and is a pathologically relevant cancer target. Further, this data also demonstrates the binding of the H460-16-2 antibody to human cancer tissues, and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

Other studies, involving the use of anti-CD44 antibodies, have limitations of therapeutic potential that are not exhibited by H460-16-2. H460-16-2 demonstrates both in vitro and in vivo anti-tumor activity. Previously described antibodies such as MAK<CD44>M-1.1.12, MAK<CD44>M-2.42.3 and MAK<CD44>M-4.3.16 have no in vitro or in vivo cytotoxicity ascribed to them and VFF-18 and Mab U36 show no intrinsic tumor cytotoxicity. In addition other anti-CD44 antibodies that have shown in vivo tumor effects also have certain limitations that are not evident with H460-16-2. For example, ASML1.1, K926, anti-CD44s and IM-78.1 show in vivo anti-tumor activity against rat, murine, rat and murine tumors grown in xenograft models respectively. H460-16-2 demonstrates anti-tumor activity in a model of human cancer. H460-16-2 is also directed against human CD44 while antibodies such as ASML1.1 recognize only rat CD44. The clone 515 anti-CD44 antibody does inhibit peritoneal tumor implantation of a human ovarian cell line but does not prevent or inhibit tumor growth. H460-16-2 is capable of inhibiting human breast tumor growth in a SCID mouse xenograft model. GKW.A3 is an anti-human CD44 monoclonal antibody capable of inhibiting tumor growth of a human metastasizing melanoma grown in mice in a preventative but not an established model. H460-16-2 has demonstrated significant anti-tumor activity in both preventative and established murine xenograft models of human breast cancer. Consequently, it is quite apparent that H460-16-2 has superior anti-tumor properties in comparison to previously described anti-CD44 antibodies. It has demonstrated both in vitro and in vivo anti-tumor activity on a human breast tumor in SCID mice and is directed against human CD44. It also exhibits activity in a preventative and established (more clinically relevant) model of human breast cancer and it exhibits activity with Cisplatin in an established model of human prostate cancer.

The present invention describes the development and use of H460-16-2 developed by the process described in patent U.S. Pat. No. 6,180,357 and identified by, its effect, in a cytotoxic assay, in tumor growth in animal models and in prolonging survival time in those suffering from cancerous disease.

This invention represents an advance in the field of cancer treatment in that it describes reagents that bind specifically to an epitope or epitopes present on the target molecule, CD44, and that directly mediate inhibition of tumor growth and metastasis in in vivo models of human liver cancer. The preponderance of evidence, disclosed herein, demonstrates that chimeric H460-16-2 mediates anti-cancer effects through ligation of epitopes present on CD44, which is expressed on liver cancer, which will broadly be understood to encompass any primary or metastatic tumor sites which arise from hepatocytes. This application demonstrates that expression of CD44 is observed with metastatic versus primary human liver cancer cell lines. This invention also discloses that chimeric H460-16-2 reduces the tumor burden and probability of metastasis of human liver cancer in vivo.

This is an advance in relation to any other previously described anti-CD44 antibody, since none have been shown to have similar properties. It also provides an advance in the field since it clearly demonstrates the direct involvement of CD44 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the H460-16-2 antigen as a target for a therapeutic agent, that when administered can reduce the tumor burden of a cancer expressing the antigen in a mammal (thus delaying disease progression) and the likelihood of metastasis of a cancer expressing the antigen in a mammal, and can also lead to a prolonged survival of the treated mammal. This invention also teaches the use of a CDMAB (H460-16-2), and its derivatives, ligands and antigen binding fragments thereof, to target its antigen to reduce the tumor burden of a cancer expressing the antigen in a mammal, and to prolong the survival of a mammal bearing tumors that express this antigen. Furthermore, this invention also teaches the use of detecting the H460-16-2 antigen in cancerous cells that can be useful for the diagnosis, prediction of therapy, and prognosis of mammals bearing tumors that express this antigen.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a summary of H460-16-2 binding on a human liver tumor and normal tissue microarray.

FIG. 7 is the tabulation of the number of different metastasis that developed with and without antibody treatment.

DETAILED DESCRIPTION OF THE INVENTION

Figure 2:
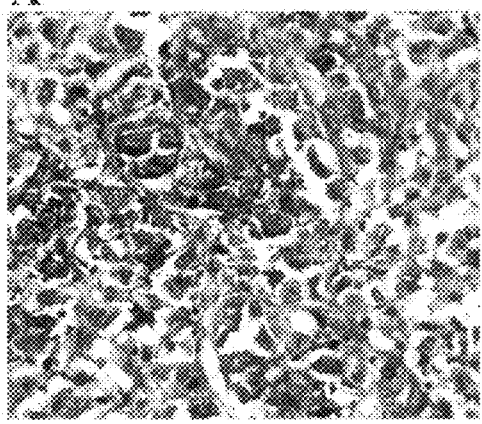
FIG. 2. Representative micrographs showing the binding pattern on liver tumor tissue obtained with H460-16-2 (A) or the isotype control antibody (B) and on non-neoplastic liver tissue obtained with H460-16-2 (C) or the isotype control antibody (D) from a human tissue microarray. H460-16-2 displayed strong positive staining for the tumor cells and was limited to staining on sinusoidal cells (black arrows) and infiltrating lymphocytes (green arrows) on the non-neoplastic liver tissue. Magnification is 200×.
Figure 2:
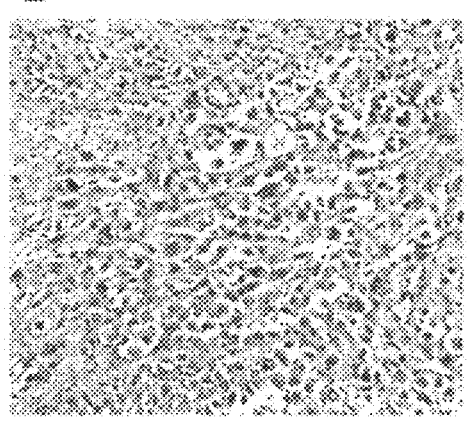
Figure 2:
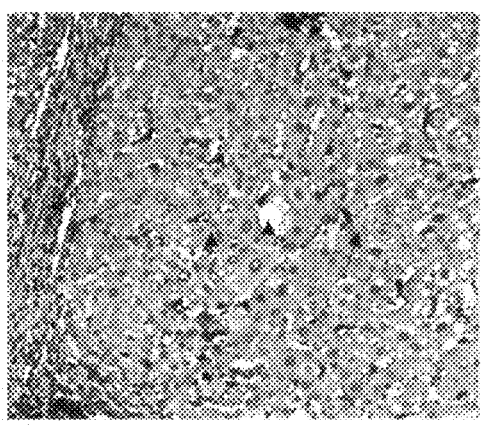
Figure 2:
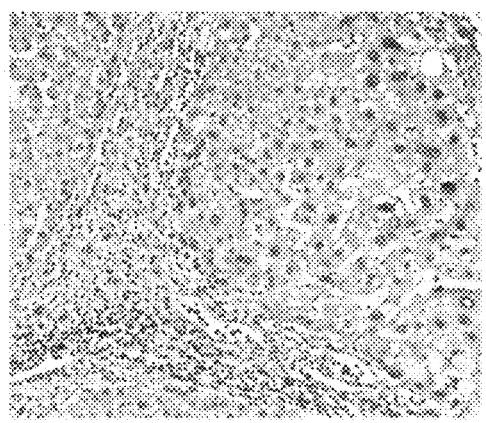

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimeric or humanized antibodies), antibody compositions with polyepitopic specificity, single-chain antibodies, diabodies, triabodies, immunoconjugates and antibody fragments (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multi-specific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and Fcγ

RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., Eur. *J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "triabodies" or "trivalent trimers" refers to the combination of three single chain antibodies. Triabodies are constructed with the amino acid terminus of a $V_L$ or $V_H$ domain, i.e., without any linker sequence. A triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. CD44 antigenic moiety, is one capable of binding that antigen with sufficient affinity such that the antibody is useful as a therapeutic or diagnostic agent in targeting a cell expressing the antigen. Where the antibody is one which binds CD44 antigenic moiety it will usually preferentially bind CD44 antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment or treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("ARA-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399-5407, 1986. They are then purified on polyacrylamide gels.

In accordance with the present invention, "humanized" and/or "chimeric" forms of non-human (e.g. murine) immunoglobulins refer to antibodies which contain specific chimeric immunoglobulins, immunoglobulin chains or fragments thereof (such as Fv, Fab, Fab', F(ab')$_2$ or other antigen-binding subsequences of antibodies) which results in the decrease of a human anti-mouse antibody (HAMA), human anti-chimeric antibody (HACA) or a human anti-human antibody (HAHA) response, compared to the original antibody, and contain the requisite portions (e.g. CDR(s), antigen binding region(s), variable domain(s) and so on) derived from said non-human immunoglobulin, necessary to reproduce the desired effect, while simultaneously retaining binding characteristics which are comparable to said non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

An antibody which induces "apoptosis" is one which induces programmed cell death by any means, illustrated by but not limited to binding of annexin V, caspase activity, fragmentation of DNA, cell shrinkage, dilation of endoplasmic reticulum, cell fragmentation, and/or formation of membrane vesicles (called apoptotic bodies).

As used herein "antibody induced cytotoxicity" is understood to mean the cytotoxic effect derived from the hybridoma supernatant or antibody produced by the hybridoma deposited with the ATCC as accession number PTA-4621, a humanized antibody of the isolated monoclonal antibody produced by the hybridoma deposited with the ATCC as accession number PTA-4621, a chimeric antibody of the isolated monoclonal antibody produced by the hybridoma deposited with the ATCC as accession number PTA-4621, antigen binding fragments, or antibody ligands thereof, which effect is not necessarily related to the degree of binding.

Throughout the instant specification, hybridoma cell lines, as well as the isolated monoclonal antibodies which are produced therefrom, are alternatively referred to by their internal designation, H460-16-2 (murine), (h)ARH460-16-2-IgG1, (ch)ARH460-16-2-IgG1, or Depository Designation, ATCC PTA-4621.

As used herein "antibody-ligand" includes a moiety which exhibits binding specificity for at least one epitope of the target antigen, and which may be an intact antibody molecule, antibody fragments, and any molecule having at least an antigen-binding region or portion thereof (i.e., the variable portion of an antibody molecule), e.g., an Fv molecule, Fab molecule, Fab' molecule, F(ab')$_2$ molecule, a bispecific antibody, a fusion protein, or any genetically engineered molecule which specifically recognizes and binds at least one epitope of the antigen bound by the isolated monoclonal antibody produced by the hybridoma cell line designated as ATCC PTA-4621 (the ATCC PTA-4621 antigen), a humanized antibody of the isolated monoclonal antibody produced by the hybridoma deposited with the ATCC as accession number PTA-4621, a chimeric antibody of the isolated monoclonal antibody produced by the hybridoma deposited with the ATCC as accession number PTA-4621, and antigen binding fragments thereof.

As used herein "cancerous disease modifying antibodies" (CDMAB) refers to monoclonal antibodies which modify the cancerous disease process in a manner which is beneficial to the patient, for example by reducing tumor burden or prolonging survival of tumor bearing individuals, and antibody-ligands thereof.

A "CDMAB related binding agent", in its broadest sense, is understood to include, but is not limited to, any form of human or non-human antibodies, antibody fragments, antibody ligands, or the like, which competitively bind to at least one CDMAB target epitope.

A "competitive binder" is understood to include any form of human or non-human antibodies, antibody fragments, antibody ligands, or the like which has binding affinity for at least one CDMAB target epitope.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents but recur up to five years, sometimes up to ten years or longer after treatment is discontinued.

Tumors that can be treated include tumors that are not vascularized, or not yet substantially vascularized, as well as vascularized tumors. Examples of solid tumors, which can be accordingly treated, include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma.

As used herein "antigen-binding region" means a portion of the molecule which recognizes the target antigen.

As used herein "competitively inhibits" means being able to recognize and bind a determinant site to which the monoclonal antibody produced by the hybridoma cell line designated as ATCC PTA-4621 (the ATCC PTA-4621 antibody), a humanized antibody of the isolated monoclonal antibody produced by the hybridoma deposited with the ATCC as accession number PTA-4621, a chimeric antibody of the isolated monoclonal antibody produced by the hybridoma deposited with the ATCC as accession number PTA-4621, antigen binding fragments, or antibody ligands thereof, is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the ATCC PTA-4621 antigen or portions thereof.

As used herein, an "immunoconjugate" means any molecule or CDMAB such as an antibody chemically or biologically linked to cytotoxins, radioactive agents, cytokines, interferons, target or reporter moieties, enzymes, toxins, anti-tumor drugs or therapeutic agents. The antibody or CDMAB may be linked to the cytotoxin, radioactive agent, cytokine, interferon, target or reporter moiety, enzyme, toxin, anti-tumor drug or therapeutic agent at any location along the molecule so long as it is able to bind its target. Examples of immunoconjugates include antibody toxin chemical conjugates and antibody-toxin fusion proteins.

Radioactive agents suitable for use as anti-tumor agents are known to those skilled in the art. For example, 131I or 211At is used. These isotopes are attached to the antibody using conventional techniques (e.g. Pedley et al., Br. J. Cancer 68, 69-73 (1993)). Alternatively, the anti-tumor agent which is attached to the antibody is an enzyme which activates a prodrug. A prodrug may be administered which will remain in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-$\alpha$). The antibody targets the cytokine to the tumor so that the cytokine mediates damage to or destruction of the tumor without affecting other tissues. The cytokine is fused to the antibody at the DNA level using conventional recombinant DNA techniques. Interferons may also be used.

As used herein, a "fusion protein" means any chimeric protein wherein an antigen binding region is connected to a biologically active molecule, e.g., toxin, enzyme, fluorescent proteins, luminescent marker, polypeptide tag, cytokine, interferon, target or reporter moiety or protein drug.

The invention further contemplates CDMAB of the present invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to the target antigen of the CDMAB of the present invention, and thereby provides a target for an anti-tumor agent or other moiety which is conjugated to avidin or streptavidin. Alternatively, biotin or another such moiety is linked to the target antigen of the CDMAB of the present invention and used as a reporter, for example in a diagnostic system where a detectable signal-producing agent is conjugated to avidin or streptavidin.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

Moreover, included within the scope of the present invention is use of the present CDMAB in vivo and in vitro for investigative or diagnostic methods, which are well known in the art. In order to carry out the diagnostic methods as contemplated herein, the instant invention may further include kits, which contain CDMAB of the present invention. Such kits will be useful for identification of individuals at risk for certain type of cancers by detecting over-expression of the CDMAB's target antigen on cells of such individuals.

Diagnostic Assay Kits

It is contemplated to utilize any suitable CDMAB in accordance with the present invention in the form of a diagnostic assay kit for determining the presence of a tumor. The tumor will generally be detected in a patient based on the presence of one or more tumor-specific antigens, e.g. proteins and/or polynucleotides which encode such proteins in a biological sample, such as blood, sera, urine and/or tumor biopsies, which samples will have been obtained from the patient.

The proteins function as markers which indicate the presence or absence of a particular tumor, for example a colon, breast, lung or prostate tumor. It is further contemplated that the antigen will have utility for the detection of other cancerous tumors. Inclusion in the diagnostic assay kits of binding agents comprised of CDMABs of the present invention, or CDMAB related binding agents, enables detection of the level of antigen that binds to the agent in the biological sample. Polynucleotide primers and probes may be used to detect the level of mRNA encoding a tumor protein, which is also indicative of the presence or absence of a cancer. In order for the binding assay to be diagnostic, data will have been generated which correlates statistically significant levels of antigen, in relation to that present in normal tissue, so as to render the recognition of binding definitively diagnostic for the presence of a cancerous tumor. It is contemplated that a plurality of formats will be useful for the diagnostic assay of the present invention, as are known to those of ordinary skill in the art, for using a binding agent to detect polypeptide markers in a sample. For example, as illustrated in Harlow and Lane, Antibodies: A Laboratory Manual, Cold Spring Harbor Laboratory, Chapters 9-14, 1988. Further contemplated are any and all combinations, permutations or modifications of the afore-described diagnostic assay formats.

The presence or absence of a cancer in a patient will typically be determined by (a) contacting a biological sample obtained from a patient with a binding agent; (b) detecting in the sample a level of polypeptide that binds to the binding agent; and (c) comparing the level of polypeptide with a predetermined cut-off value.

In an illustrative embodiment, it is contemplated that the assay will involve the use of a CDMAB based binding agent immobilized on a solid support to bind to and remove the polypeptide from the remainder of the sample. The bound polypeptide may then be detected using a detection reagent that contains a reporter group and specifically binds to the binding agent/polypeptide complex. Illustrative detection reagents may include a CDMAB based binding agent that specifically binds to the polypeptide or an antibody or other agent that specifically binds to the binding agent, such as an anti-immunoglobulin, protein G, protein A or a lectin. In an alternative embodiment, it is contemplated that a competitive assay may be utilized, in which a polypeptide is labeled with a reporter group and allowed to bind to the immobilized binding agent after incubation of the binding agent with the sample. Indicative of the reactivity of the sample with the immobilized binding agent, is the extent to which components of the sample inhibit the binding of the labeled polypeptide to the binding agent. Suitable polypeptides for use within such assays include full length tumor-specific proteins and/or portions thereof, to which the binding agent has binding affinity.

The diagnostic kit will be provided with a solid support which may be in the form of any material known to those of ordinary skill in the art to which the protein may be attached. Suitable examples may include a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

It is contemplated that the binding agent will be immobilized on the solid support using a variety of techniques known to those of skill in the art, which are amply described in the patent and scientific literature. The term "immobilization" refers to both noncovalent association, such as adsorption, and covalent attachment, which, in the context of the present invention, may be a direct linkage between the agent and functional groups on the support, or may be a linkage by way of a cross-linking agent. In a preferred, albeit non-limiting embodiment, immobilization by adsorption to a well in a microtiter plate or to a membrane is preferable. Adsorption may be achieved by contacting the binding agent, in a suitable buffer, with the solid support for a suitable amount of time. The contact time may vary with temperature, and will generally be within a range of between about 1 hour and about 1 day.

Covalent attachment of binding agent to a solid support would ordinarily be accomplished by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner.

It is further contemplated that the diagnostic assay kit will take the form of a two-antibody sandwich assay. This assay may be performed by first contacting an antibody, e.g. the instantly disclosed CDMAB that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

In a specific embodiment, it is contemplated that once the antibody is immobilized on the support as described above, the remaining protein binding sites on the support will be blocked, via the use of any suitable blocking agent known to those of ordinary skill in the art, such as bovine serum albumin or Tween 20™ (Sigma Chemical Co., St. Louis, Mo.). The immobilized antibody would then be incubated with the sample, and polypeptide would be allowed to bind to the antibody. The sample could be diluted with a suitable diluent, such as phosphate-buffered saline (PBS) prior to incubation. In general, an appropriate contact time (i.e., incubation time) would be selected to correspond to a period of time sufficient to detect the presence of polypeptide within a sample obtained from an individual with the specifically selected tumor. Preferably, the contact time is sufficient to achieve a level of binding that is at least about 95 percent of that achieved at equilibrium between bound and unbound polypeptide. Those of ordinary skill in the art will recognize that the time necessary to achieve equilibrium may be readily determined by assaying the level of binding that occurs over a period of time.

It is further contemplated that unbound sample would then be removed by washing the solid support with an appropriate buffer. The second antibody, which contains a reporter group, would then be added to the solid support. Incubation of the detection reagent with the immobilized antibody-polypeptide complex would then be carried out for an amount of time sufficient to detect the bound polypeptide. Subsequently, unbound detection reagent would then be removed and bound detection reagent would be detected using the reporter group. The method employed for detecting the reporter group is necessarily specific to the type of reporter group selected, for example for radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

In order to utilize the diagnostic assay kit of the present invention to determine the presence or absence of a cancer, such as prostate cancer, the signal detected from the reporter group that remains bound to the solid support would generally be compared to a signal that corresponds to a predetermined cut-off value. For example, an illustrative cut-off value for the detection of a cancer may be the average mean signal obtained when the immobilized antibody is incubated with samples from patients without the cancer. In general, a sample generating a signal that is about three standard deviations above the predetermined cut-off value would be considered positive for the cancer. In an alternate embodiment, the cut-off value might be determined by using a Receiver Operator Curve, according to the method of Sackett, Clinical Epidemiology. A Basic Science for Clinical Medicine, Little Brown and Co., 1985, p. 106-7. In such an embodiment, the cut-off value could be determined from a plot of pairs of true positive rates (i.e., sensitivity) and false positive rates (100 percent-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

It is contemplated that the diagnostic assay enabled by the kit will be performed in either a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound will be immersed in a solution containing the sample. The sample migrates along the membrane through a region containing second binding agent and to the area of immobilized binding agent. Concentration of the second binding agent at the area of immobilized antibody indicates the presence of a cancer. Generation of a pattern, such as a line, at the binding site, which can be read visually, will be indicative of a positive test. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in the instant diagnostic assay are the instantly disclosed antibodies, antigen-binding fragments thereof, and any CDMAB related binding agents as herein described. The amount of antibody immobilized on the membrane will be any amount effective to produce a diagnostic assay, and may range from about 25 nanograms to about 1 microgram. Typically such tests may be performed with a very small amount of biological sample.

Additionally, CDMABs of the present invention may be used in the laboratory for research due to its ability to identify its target antigen.

In order that the invention herein described may be more fully understood, the following description is set forth.

The present invention provides CDMABs (i.e., ATCC PTA-4621 CDMAB, a humanized antibody of the isolated monoclonal antibody produced by the hybridoma deposited with the ATCC as accession number PTA-4621, a chimeric antibody of the isolated monoclonal antibody produced by the hybridoma deposited with the ATCC as accession number PTA-4621, antigen binding fragments, or antibody ligands thereof) which specifically recognize and bind the ATCC PTA-4621 antigen.

The CDMABs of the isolated monoclonal antibody produced by the hybridoma deposited with the ATCC as accession number PTA-4621 may be in any form as long as it has an antigen-binding region which competitively inhibits the immunospecific binding of the isolated monoclonal antibody produced by hybridoma ATCC PTA-4621 to its target antigen. Thus, any recombinant proteins (e.g., fusion proteins wherein the antibody is combined with a second protein such as a lymphokine or a tumor inhibitory growth factor) having the same binding specificity as the ATCC PTA-4621 antibody fall within the scope of this invention.

In one embodiment of the invention, the CDMAB is the ATCC PTA-4621 antibody.

In other embodiments, the CDMAB is an antigen binding fragment which may be a Fv molecule (such as a single-chain Fv molecule), a Fab molecule, a Fab' molecule, a F(ab')$_2$ molecule, a fusion protein, a bispecific antibody, a heteroantibody or any recombinant molecule having the antigen-binding region of the ATCC PTA-4621 antibody. The CDMAB of the invention is directed to the epitope to which the ATCC PTA-4621 monoclonal antibody is directed.

The CDMAB of the invention may be modified, i.e., by amino acid modifications within the molecule, so as to produce derivative molecules. Chemical modification may also be possible. Modification by direct mutation, methods of affinity maturation, phage display or chain shuffling may also be possible.

Affinity and specificity can be modified or improved by mutating CDR and/or phenylalanine tryptophan (FW) residues and screening for antigen binding sites having the desired characteristics (e.g., Yang et al., J. Mol. Biol., (1995) 254: 392-403). One way is to randomize individual residues or combinations of residues so that in a population of otherwise identical antigen binding sites, subsets of from two to twenty amino acids are found at particular positions. Alternatively, mutations can be induced over a range of residues by error prone PCR methods (e.g., Hawkins et al., J. Mol. Biol., (1992) 226: 889-96). In another example, phage display vectors containing heavy and light chain variable region genes can be propagated in mutator strains of E. coli (e.g., Low et al., J. Mol. Biol., (1996) 250: 359-68). These methods of mutagenesis are illustrative of the many methods known to one of skill in the art.

Another manner for increasing affinity of the antibodies of the present invention is to carry out chain shuffling, where the heavy or light chain are randomly paired with other heavy or light chains to prepare an antibody with higher affinity. The various CDRs of the antibodies may also be shuffled with the corresponding CDRs in other antibodies.

Derivative molecules would retain the functional property of the polypeptide, namely, the molecule having such substitutions will still permit the binding of the polypeptide to the IDAC 051206-01 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

EXAMPLE 1

Human Liver Tumor Tissue Staining

IHC studies were conducted to further evaluate the binding of H460-16-2 to human liver tumor tissue. IHC optimization studies were performed previously in order to determine the conditions for further experiments. H460-16-2 monoclonal antibodies were produced and purified as previously disclosed in Ser. No. 10/603,000.

Binding of antibodies to 49 human liver tumor and 9 normal liver tissues was performed using a human, liver normal and tumor tissue microarray (Imgenex, San Diego, Calif.). The following information was provided for each patient: age, sex, organ and diagnosis. Tissue sections were deparaffinized by drying in an oven at 58° C. for 1 hour and dewaxed by immersing in xylene 5 times for 4 minutes each in Coplin jars. Following treatment through a series of graded ethanol washes (100 percent-75 percent) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3 percent hydrogen peroxide solution for 6 minutes, washed with PBS three times for 5 minutes each, dried, incubated with Universal blocking solution (Dako, Toronto, Ontario) for 5 minutes at room temperature. H460-16-2, anti-AFP (alpha 1 fetoprotein; clone AFP-11, Abcam, Cambridge, Mass.) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 micrograms/mL for each antibody except for anti-PSMA which was diluted to 10 micrograms/mL) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100 percent) and cleared with xylene. Using mounting media (Dako Faramount, Toronto, Ontario) the slides were coverslipped. Slides were microscopically examined using an Axiovert 200 (Ziess Canada, Toronto, ON) and digital images acquired and stored using Northern Eclipse Imaging Software (Mississauga, ON). Results were read, scored and interpreted by a histopathologist.

As disclosed in FIG. 1, the H460-16-2 antibody showed binding to 21/49 (43 percent) of tested liver cancers, including 11/37 (30 percent) of primary, 7/8 (88 percent) of metastatic hepatocellular carcinoma, 1/2 (50 percent) of primary and 2/2 (100 percent) of metastatic cholangiocarcinomas. The antibody showed significant higher binding to advanced tumors' stages III and IV in comparison with early stages I and II (p=0.03) [stage I, 0/2 (0 percent); stage II, 2/17 (12 percent); stage III, 8/16 (50 percent) and stage IV, 6/8 (75 percent)]. H460-16-2 was specific for tumor cells and infiltrating inflammatory cells. Cellular localization was mainly membranous. Some tumors also displayed a diffuse cytoplasmic staining pattern. The antibody bound to 9/9 of non-neoplastic liver tissues (FIG. 2). However, the binding was restricted to the sinusoidal cells and infiltrating lymphocytes. The H460-16-2 antigen appears to be specifically expressed on advanced liver tumor tissue. H460-16-2 therefore has potential as a therapeutic drug in the treatment of liver cancer.

Therefore, the H460-16-2 antigen appears to be expressed on liver tumor tissue with binding preference for metastatic and advanced liver tumor tissue. H460-16-2 therefore has utility as a diagnostic reagent for hepatocellular carcinoma, and as a therapeutic drug in the treatment of liver cancer.

EXAMPLE 2

Correlation of CD44 with Metastatic Potential of Various HCC Cell Lines

To further evaluate this correlation in vitro, six heptaocellular carcinoma (HCC) cell lines with various metastatic potential (Hep3B (American Type Culture Collection, Manassas, Va.), Huh-7 (a gift from Dr. H. Nakabayashi, Hokkaido University School of Medicine, Sapporo, Japan), PLC (Japanese Cancer Research Bank, Tokyo, Japan), MHCC-97L, MHCC-97H and HCCLM3 (Liver Cancer Institute, Fudan University, Shanghai, China)) were evaluated for CD44 expression by flow cytometry using (ch)ARH460-16-2-IgG1 antibody. To detect expression of CD44 in various HCC cell lines, cells were stained for 1 hour with (ch)ARH460-16-2-IgG1 or isotype control antibody (10 micrograms/mL) and 30 minutes with the appropriate secondary antibody and analyzed by FACS.

Figure 3:
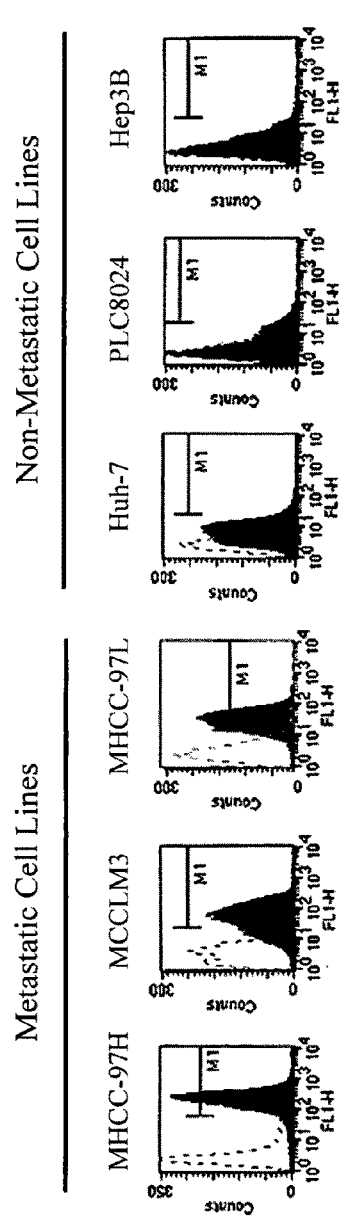
FIG. 3 demonstrates the correlation between CD44 overexpression and the metastatic potential of various HCC cell lines.

By flow cytometry, CD44 expression levels were found to be higher in the metastatic HCC cell lines (MHCC-97L, HCCLM3 and MHCC-97H) when compared with the primary non-metastatic cell lines (Hep3B, Huh-7 and PLC) (FIG. 3).

EXAMPLE 3

Orthotopic HCC Tumor Model with HCCLM3 Cells

Luciferase Labeling of Cells

To further evaluate this correlation in vivo, (ch)ARH460-16-2-IgG1 was tested in an orthotopic HCC tumor model. For the luciferase labelling of HCCLM3 (a metastatic HCC cell line Yang et al., Cancer Genet. Cytogenet. 158(2):180-183 2005) cells, lentiviral vector harboring the luciferase gene was constructed and transfected into the cells using the method described previously (Cheung et al., Cancer Res. 66(8):4357-4367 2006). Stable transfectants were generated from a pool of greater than 20 positive clones (which were selected with blasticidin at a concentration of 2 micrograms/mL).

Animal CCD Experiments

One million HCCLM3 luciferase labeled cells were subcutaneously injected into the right flank of nude mice, which were then observed daily for signs of tumor development. Once the tumors reached 1 to 1.5 cm in diameter, it was removed and cut into about 1- to 2-mm cubes, which were then subsequently implanted into the left liver lobe of 5 week old male nude mice. Ten days later, the nude mice were randomized into a group of four and were treated either with isotype control or 2, 10 or 20 mg/kg (ch)ARH460-16-2-IgG1. (ch)ARH460-16-2-IgG1 test antibody was administered intraperitoneally to each cohort, in a volume of 200 microliters after dilution from the stock concentration with a diluent that contained 2.7 mM KCl, 1 mM $KH_2PO_4$, 137 mM NaCl and 20 mM $Na_2HPO_4$. The antibodies were then administered 2 times per week for a total of 12 doses in the same fashion until day 45 post-implantation.

The mice were imaged on day 7 and day 45 after tumor inoculation. Mice were anesthetized with a ketamine-xylazine mix in a 4:1 ratio according to the Committee on the Use of Live Animals in Teaching and Research of the University of Hong Kong.

Imaging was done using a Xenogen IVIS 100 cooled CCD camera (Xenogen, New Jersey, USA). The mice were injected with 200 microliters of 15 mg/mL D-luciferin intraperitoneally for 15 minutes before imaging after which they were placed in a light-tight chamber. A gray-scale reference image was obtained followed by the acquisition of a bioluminescent image. The acquisition time ranged from 3 seconds to 1 minute. The images shown are pseudoimages of the emitted light in photons/s/cm2/steradian, superimposed over the gray-scale photographs of the animal.

Figure 4:
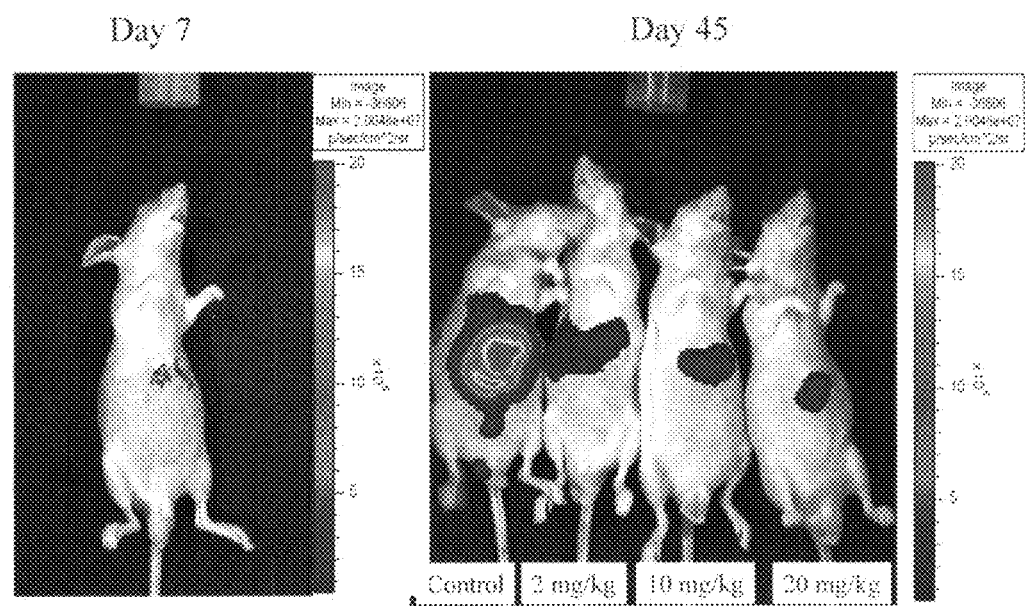
FIG. 4 demonstrates the effect of (ch)ARH460-16-2-IgG1 on HCC tumor growth and metastasis in an established orthotopic HCC tumor model. Data points represent the mean +/−SEM.
Figure 5:
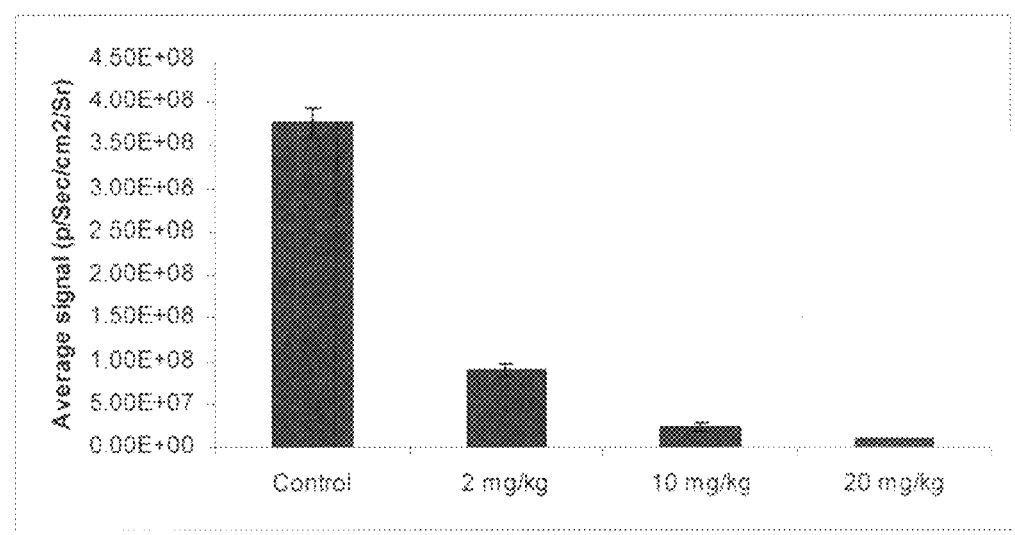
FIG. 5 demonstrates the quantitative effect of (ch) ARH460-16-2-IgG1 on tumor growth in an established orthotopic HCC tumor model. The bar graph summarizes the average basal signal of tumors from four groups of animals in photons/s/cm$^2$/steridian. Each column represents the average basal level signals on day 45 following tumor inoculation.
Figure 6:
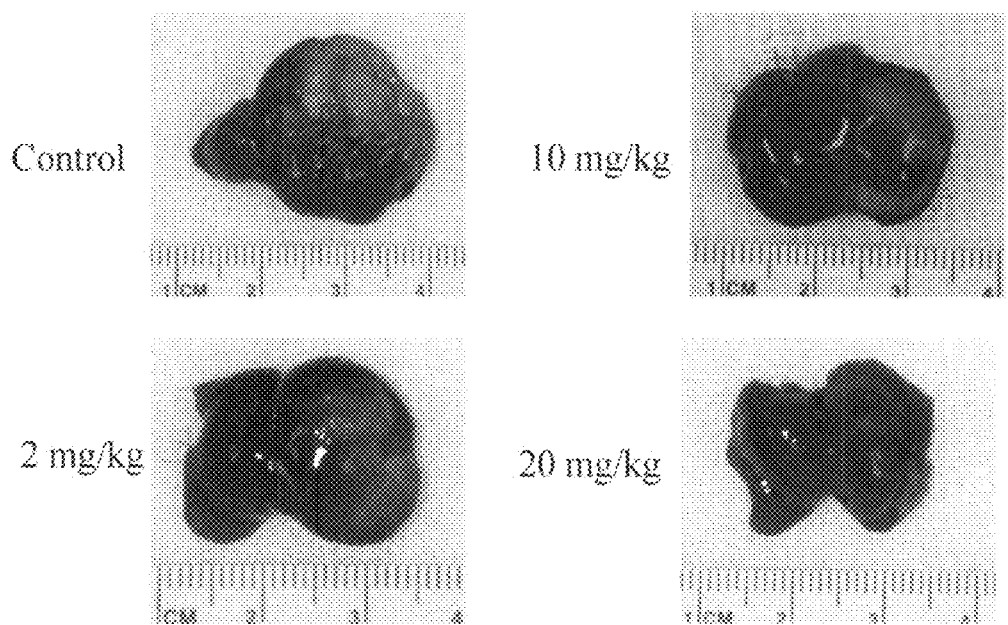
FIG. 6 visually demonstrates the effect of (ch)ARH460-16-2-IgG1 on primary tumor growth in an established orthotopic HCC tumor model.

(ch)ARH460-16-2-IgG1 significantly reduced tumor burden in an established model of human HCC (FIG. 4). On day 45 after tumor implantation, (ch)ARH460-16-2-IgG1 decreased primary liver tumor signal from 37.6E+7±0.17 to 9E+7±0.72, 2.3 E+7±0.52 and 0.1E+7±0.5 at the doses of 2, 10 and 20 mg/kg, respectively (FIG. 5). Representative primary tumors from the different groups were also photographed (FIG. 6). There was no significant difference in mean body weight between the two groups over the course of the study.

(ch)ARH460-16-2-IgG1 significantly suppressed intrahepatic and lung metastases in an established orthotopic model of human HCC. The number of mice with lung and intrahepatic metastases in the treatment group and control group are shown in FIG. 7. (ch)ARH460-16-2-IgG1 significantly suppressed intrahepatic metastasis from (5/5) 100 percent to (2/5) 40 percent at a dose of 2 mg/kg. (ch)ARH460-16-2-IgG1 also significantly suppressed lung metastasis from (5/5) 100 percent to (0/5) 0 percent at a dose of 2 mg/kg (FIG. 7). Besides the liver and lung metastasis, control groups also showed intestine (4/5) and urinary (3/5) metastasis.

In summary, (ch)ARH460-16-2-IgG1 was well-tolerated, decreased the tumor burden and intrahepatic and lung metastases in this established human orthotopic HCC tumor model.

The preponderance of evidence shows that murine and chimeric H460-16-2 mediates anti-cancer effects through ligation of epitopes present on CD44, which is expressed on liver cancer. It has been shown that higher expression of CD44 is observed with metastatic versus primary human liver cancer cell lines. It has also been shown that chimeric H460-16-2 reduces the tumor burden and probability of metastasis of human liver cancer in vivo. Therefore, chimeric H460-16-2 has therapeutic potential for the diagnosis and treatment of liver cancer, broadly understood to include any primary or metastatic tumor sites which arise from hepatocytes.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating primary breast, prostate or melanoma human tumor sites and metastatic sites in a mammal, wherein said primary breast, prostate or melanoma human tumor or metastasis expresses an epitope of the CD44 antigen which is specifically bound by the isolated monoclonal antibody produced by the hybridoma deposited with the ATCC as accession number PTA-4621 or an antigen binding fragment produced from the monoclonal antibody, wherein said antigen binding fragment is characterized by an ability to competitively inhibit binding of said isolated monoclonal antibody to its target epitope, comprising administering to said mammal said isolated monoclonal antibody or said antigen binding fragment thereof in an amount effective to result in a reduction of said mammal's tumor burden.

2. The method of claim 1 wherein said isolated monoclonal antibody or said antigen binding fragment thereof is conjugated to a cytotoxic moiety.

3. The method of claim 2, wherein said cytotoxic moiety is a radioactive isotope.

4. The method of claim 1 wherein said isolated monoclonal antibody activates complement.

5. The method of claim 1 wherein said isolated monoclonal antibody mediates antibody dependent cellular cytotoxicity.

6. The method of claim 1 wherein said isolated monoclonal antibody is a humanized antibody of the isolated monoclonal antibody produced by the hybridoma deposited with the ATCC as accession number PTA-4621 or an antigen binding fragment produced from the humanized antibody.

7. The method of claim 1 wherein said isolated monoclonal antibody is a chimeric antibody of the isolated monoclonal antibody produced by the hybridoma deposited with the ATCC as accession number PTA-4621 or an antigen binding fragment produced from the chimeric antibody.

8. A method of treating primary human breast, prostate or melanoma tumor sites and metastatic sites susceptible to antibody induced cellular cytotoxicity in a mammal, wherein said primary human breast, prostate or melanoma tumor or metastasis expresses an epitope of the CD44 antigen which is specifically bound by the isolated monoclonal antibody produced by the clone hybridoma deposited with the ATCC as accession number PTA-4621 or an antigen binding fragment produced from the monoclonal antibody, wherein said antigen binding fragment is characterized by an ability to competitively inhibit binding of said isolated monoclonal antibody or antigen binding fragment thereof to its target antigen, comprising administering to said mammal said isolated monoclonal antibody or said antigen binding fragment thereof in an amount effective to result in a reduction of said mammal's tumor burden.

9. The method of claim 8 wherein said isolated monoclonal antibody or said antigen binding fragment thereof is conjugated to a cytotoxic moiety.

10. The method of claim 8 wherein said cytotoxic moiety is a radioactive isotope.

11. The method of claim 8 wherein said isolated monoclonal antibody activates complement.

12. The method of claim 8 wherein said isolated monoclonal antibody mediates antibody dependent cellular cytotoxicity.

13. The method of claim 8 wherein said isolated monoclonal antibody is a humanized antibody of the isolated monoclonal antibody produced by the hybridoma deposited with the ATCC as accession number PTA-4621 or an antigen binding fragment produced from the humanized antibody.

14. The method of claim 8 wherein said isolated monoclonal antibody is a chimeric antibody of the isolated monoclonal antibody produced by the hybridoma deposited with the ATCC as accession number PTA-4621 or an antigen binding fragment produced from the chimeric antibody.

15. A process for treating human breast, prostate or melanoma cancerous tumors in a patient, which express an epitope or epitopes of human CD44 antigen which is specifically bound by the isolated monoclonal antibody produced by hybridoma cell line H460-16-2 having ATCC Accession No. PTA-4621, comprising:
    administering to said patient in need thereof, at least one isolated monoclonal antibody or an antigen binding fragment produced from the monoclonal antibody that recognizes the same epitope or epitopes as those recognized by the isolated monoclonal antibody produced by hybridoma cell line H460-16-2 having ATCC Accession No. PTA-4621;
    wherein binding of said epitope or epitopes results in a reduction of tumor burden.

16. A process for treating human breast, prostate or melanoma cancerous tumors which express an epitope or epitopes of human CD44 antigen which is specifically bound by the isolated monoclonal antibody produced by hybridoma cell line H460-16-2 having ATCC Accession No. PTA-4621, comprising:
    administering to a patient in need thereof, at least one isolated monoclonal antibody or an antigen binding fragment produced from the monoclonal antibody that recognizes the same epitope or epitopes as those recognized by the isolated monoclonal antibody produced by hybridoma cell line H460-16-2 having ATCC Accession No. PTA-4621;
    wherein said administration results in a reduction of tumor burden.

* * * * *

UNITED STATES PATENT AND TRADEMARK OFFICE
CERTIFICATE OF CORRECTION

PATENT NO. : 8,048,416 B2  
APPLICATION NO. : 11/786165  
DATED : November 1, 2011  
INVENTOR(S) : Young et al.

Page 1 of 1

It is certified that error appears in the above-identified patent and that said Letters Patent is hereby corrected as shown below:

Title page Item (63) Col. 1 (Related U.S. Application Data), Line 9, delete "7,187,397," and insert -- 7,189,397, --

Signed and Sealed this  
Seventeenth Day of January, 2012

David J. Kappos  
*Director of the United States Patent and Trademark Office*